United States Patent [19]

Mills et al.

[11] 4,391,826

[45] Jul. 5, 1983

[54] PHENETHANOLAMINES, COMPOSITIONS CONTAINING THE SAME, AND METHOD FOR EFFECTING WEIGHT CONTROL

[75] Inventors: Jack Mills; Klaus K. Schmiegel; Walter N. Shaw, all of Indianapolis, Ind.

[73] Assignee: Eli Lilly and Company, Indianapolis, Ind.

[21] Appl. No.: 96,361

[22] Filed: Nov. 21, 1979

Related U.S. Application Data

[63] Continuation-in-part of Ser. No. 921,670, Jul. 3, 1978, abandoned.

[51] Int. Cl.³ ............................................. A01N 37/18
[52] U.S. Cl. .................................... 424/324; 424/309; 424/311; 424/315; 424/316; 424/330; 560/42; 560/142; 564/165; 564/363
[58] Field of Search .................... 260/559 A; 424/324, 424/315, 316; 564/165

[56] References Cited

U.S. PATENT DOCUMENTS

| | | | |
|---|---|---|---|
| 3,056,836 | 10/1962 | Moed | 260/570.7 R X |
| 3,723,524 | 3/1973 | Augstein et al. | 260/559 A X |
| 3,911,008 | 10/1975 | Edinberry et al. | 260/559 A |
| 4,032,575 | 6/1977 | Ikezaki et al. | 260/570.6 |
| 4,041,074 | 8/1977 | Main | 260/556 AR |
| 4,048,229 | 9/1977 | Colella et al. | 260/570.6 |
| 4,086,272 | 4/1978 | Cox et al. | 260/559 A X |
| 4,101,579 | 7/1978 | Hartley et al. | 260/559 A |
| 4,146,638 | 3/1979 | Renth et al. | 260/559 A X |
| 4,165,384 | 8/1979 | Carlsson et al. | 260/559 A X |

FOREIGN PATENT DOCUMENTS

| | | |
|---|---|---|
| 894396 | 9/1953 | Fed. Rep. of Germany . |
| 6481871 | 8/1965 | Netherlands . |
| 6610530 | 1/1968 | Netherlands . |
| 673994 | 3/1967 | South Africa . |

OTHER PUBLICATIONS

Van Dijk et al., Recueil, vol. 92, pp. 1281–1297 (1973).
Moed et al., Recueil, vol. 74, pp. 919–936 (1955).
Richards et al., Br. J. Clin. Pharmac., (1974), pp. 505–510.
Arch. Path. u. Pharmakol, Bd. 213, S-283-313 (1951).

Primary Examiner—Charles F. Warren
Attorney, Agent, or Firm—Charles W. Ashbrook; Arthur R. Whale

[57] ABSTRACT

Optically active N-3-(4-substituted phenyl)propyl-β-phenethanolamines are provided as well as pharmaceutical compositions containing such compounds. A method for effecting weight control in obese animals utilizing optically active phenethanolamines is disclosed. Novel intermediates useful in the preparation of optically active β-phenethanolamines are provided.

20 Claims, No Drawings

PHENETHANOLAMINES, COMPOSITIONS CONTAINING THE SAME, AND METHOD FOR EFFECTING WEIGHT CONTROL

CROSS-REFERENCE TO RELATED CASES

This is a continuation-in-part of Ser. No. 921,670, filed July 3, 1978, now abandoned.

BACKGROUND OF THE INVENTION

This invention relates to a group of compounds generally referred to as phenethanolamines. The compounds provided are unique since they are effective in the treatment of obesity yet are essentially devoid of cardiac effects.

Some of the most extensive efforts in basic research have been in the area of β-phenylethylamine derivatives, many of which are catecholamines. A great deal of study, for example, has been carried out on the naturally occurring catecholamine epinephrine. Epinephrine is a potent sympathomimetic drug and a powerful cardiac stimulant. The use of epinephrine is limited, however, due to its undesirable side effects, which include fear, anxiety, tremor, tenseness, throbbing headache, increased blood pressure, dizziness, respiratory difficulty and palpitation, as well as its short duration of action.

The use of drugs which cause more than one biological effect can be very dangerous for the biological system. For example, since both bronchodilation and cardiac stimulation are mediated by the broad group of receptors known as β-receptors, a drug acting on such β-receptors not only would effect bronchodilation, but additionally could cause observable effects upon the heart. In fact, some individuals allegedly have died from ventricular fibrillation caused by excessive β-stimulation after using bronchodilation agents; (See Greenburg and Pines, *Br. Med. J.* 1, 563(1967).

Since β-phenethylamine type compounds are known to have a variety of pharmacological activities, considerable research has been devoted to achieving a separation of the various biological effects of such agents. It now has been found that by selecting a unique group of N-phenylpropyl phenethanolamines, and by separating the optical isomers of certain of such compounds, a unique and unexpected degree of lipolytic activity with little or no cardiac stimulatory activity surprisingly is achieved. The discovery of compounds having a separation of cardiac activity from lipolytic activity permits the chronic administration of such lipolytic agents to obese animals so that weight control is effected by loss of adipose tissue, or prevention of the formation thereof, without accompanying adverse cardiac effects.

SUMMARY OF THE INVENTION

This invention relates to particular phenethanolamine derivatives which are useful as antiobesity agents. More specifically, the invention provides certain optically active compounds selected from the group of phenethanolamine bases represented by the general formula

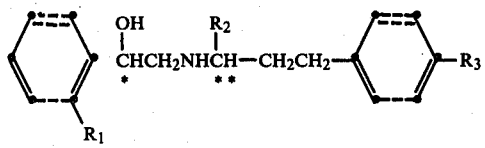

wherein:
$R_1$ is hydrogen or fluorine;
$R_2$ is hydrogen, methyl or ethyl;
$R_3$ is hydroxy, $C_1$–$C_4$ alkanoyloxy, aminocarbonyl, methylaminocarbonyl, or $C_1$–$C_2$ alkoxycarbonyl;
with the limitation that when $R_2$ is hydrogen, $R_3$ is aminocarbonyl, methylaminocarbonyl or $C_1$–$C_2$ alkoxycarbonyl;
$\overset{*}{C}$ is an asymmetric carbon atom having the R absolute stereochemical configuration;
$\overset{**}{C}$ is an asymmetric carbon atom when $R_2$ is methyl or ethyl, and when asymmetric is of the S absolute stereochemical configuration; and
the non-toxic pharmaceutically acceptable acid addition salts thereof.

A preferred group of compounds have the above formula wherein $R_2$ is methyl.

Another preferred group are those wherein $R_2$ is hydrogen.

More preferred compounds are those wherein $R_2$ is methyl or ethyl and $R_3$ is hydroxy, aminocarbonyl, methylaminocarbonyl or $C_1$–$C_2$ alkoxycarbonyl, and the pharmaceutically acceptable acid addition salts thereof.

Additionally preferred compounds have the above formula wherein $R_1$ is hydrogen, $R_2$ is methyl and $R_3$ is hydroxy, methoxycarbonyl, aminocarbonyl or methylaminocarbonyl.

The most preferred compounds of the invention have the above formula wherein $R_1$ is hydrogen, $R_2$ is methyl, $R_3$ is hydroxy or aminocarbonyl, and the pharmaceutically acceptable salts thereof.

A further embodiment of this invention is a pharmaceutical formulation useful for controlling weight in an obese mammal comprising an amount effective for causing weight control of at least one phenethanolamine having the above formula in combination with a pharmaceutically acceptable diluent or carrier therefor. Preferred formulations comprise a compound of the above formula wherein $R_2$ is methyl, as well as those wherein $R_2$ is hydrogen. Another preferred formulation is one containing a phenethanolamine of the above formula wherein $R_2$ is methyl or ethyl and $R_3$ is hydroxy, aminocarbonyl, methylaminocarbonyl or $C_1$–$C_2$ alkoxycarbonyl, or a salt thereof. An especially preferred pharmaceutical formulation comprises an amount effective for causing weight loss in an obese subject of an R,S phenethanolamine of the above formula wherein $R_1$ is hydrogen, $R_2$ is methyl and $R_3$ is hydroxy, aminocarbonyl, methylaminocarbonyl or methoxycarbonyl, and most preferably wherein $R_3$ is hydroxy or aminocarbonyl.

This invention additionally provides a method for controlling obesity in obese animals which comprises administering to an obese subject an amount effective for controlling weight of an optically active phenethanolamine having the above formula, or a pharmaceutically acceptable acid addition salt thereof. A preferred method of treatment comprises administering to a subject in need of treatment an effective dose of a compound having the above formula wherein $R_2$ is methyl. Another preferred method of treatment comprises administering a compound of the above formula wherein $R_2$ is methyl or ethyl and $R_3$ is hydroxy, aminocarbonyl, methylaminocarbonyl or $C_1$-$C_2$ alkoxycarbonyl, or a pharmaceutically acceptable salt thereof. A further preferred method of treatment comprises administering an effective dose of a compound of the above formula wherein $R_1$ is hydrogen, $R_2$ is methyl and $R_3$ is hydroxy, aminocarbonyl, methylaminocarbonyl or methoxycarbonyl, most preferably hydroxy or aminocarbonyl, or a pharmaceutically acceptable salt thereof.

A particularly preferred method of treatment provided by this invention is the weight control in animals utilized for the production of meat for human consumption. Compounds of the invention, especially those of the above formula wherein $R_2$ is hydrogen, are particularly useful in improving the meat quality, for example leanness, of meat producing animals such as swine, poultry and bovine. A further preferred method of treatment provided by this invention comprises administering to swine for improving meat quality a compound of the above formula wherein $R_2$ is hydrogen.

In an additional embodiment of this invention, there is provided an intermediate which is useful in the synthesis of the R,S phenethanolamines defined by the above formula wherein $R_2$ is methyl or ethyl. Such intermediates are S-1-methyl(or ethyl)-3-(substituted phenyl)propylamines of the formula

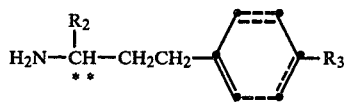

wherein:

$R_2$ is methyl or ethyl;

$R_3$ is hydroxy, $C_1$-$C_4$ alkanoyloxy, aminocarbonyl, methylaminocarbonyl, or $C_1$-$C_2$ alkoxycarbonyl; and $\overset{**}{C}$ is an asymmetric carbon atom having the S absolute stereochemical configuration.

Still another embodiment of this invention is a novel process for preparing an R,S phenethanolamine of the above formula, wherein $R_2$ is methyl or ethyl, comprising condensing an optically active R-styrene oxide of the formula

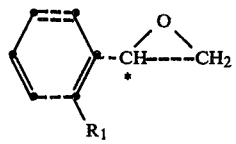

with an optically active S-propyl amine of the formula

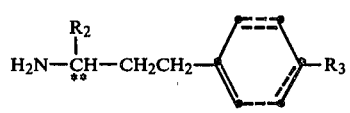

wherein:

$R_1$ is hydrogen or fluorine;

$R_2$ is methyl or ethyl; and $R_3$ is hydroxy, $C_1$-$C_4$ alkanoyloxy, aminocarbonyl, methylaminocarbonyl, or $C_1$-$C_2$ alkoxycarbonyl.

DETAILED DESCRIPTION OF THE INVENTION

While the compounds provided by this invention are referred to generically as phenethanolamines, they will be systematically named herein as N-substituted-3-phenylpropylamines. For example, a compound having the above formula wherein $R_1$ and $R_2$ both are hydrogen and $R_3$ is aminocarbonyl will be named herein as: N-(2-phenyl-2-hydroxyethyl)-3-(4-aminocarbonylphenyl)propylamine.

The compounds of the invention always will have at least one asymmetric carbon atom, namely the carbon atom labeled "$\overset{*}{C}$" in the above formula. The stereochemical configuration of the compounds of this invention will be designated according to the R and S nomenclature. A full discussion of such system of naming is presented by Cahn et al., Experientia, Vol. XII, pp. 81–124 (1956). Accordingly, the stereochemical configuration of the carbon atom labeled "$\overset{*}{C}$" will be designated as R and will be presented first when naming the compounds comprehended by this invention. The compound referred to above will therefore more accurately be named as: R-N-(2-phenyl-2-hydroxyethyl)-3-(4-aminocarbonylphenyl)propylamine.

Preferred compounds of the invention are those wherein $R_2$ is methyl or ethyl, and such compounds have two asymmetric centers. The asymmetric carbon atom labeled "$\overset{**}{C}$" has the S absolute stereochemical configuration according to this invention. Such fact is designated in the systematic naming of such compounds as illustrated for the compound of the above formula wherein $R_1$ is hydrogen, $R_2$ is methyl and $R_3$ is aminocarbonyl: R,S-N-(2-phenyl-2-hydroxyethyl)-1-methyl-3-(4-aminocarbonylphenyl)propylamine.

The compounds provided by this invention can be prepared by any of a number of methods involving well known and routinely used chemical processes. A novel and preferred process involves the reaction of an optically active styrene oxide with a 3-phenylpropylamine (where $R_2$ is hydrogen) or with an optically active 1-alkyl-3-phenylpropylamine (when $R_2$ is methyl or ethyl). For example, an optically active styrene oxide such as R-ortho-fluorostyrene oxide can be reacted with approximately a equimolar quantity of an optically active phenylpropylamine such as S-1-methyl-3-(4-methylaminocarbonylphenyl)propylamine to provide the corresponding optically active phenethanolamine of this invention, namely R,S-N-[2-(2-fluorophenyl)-2-hydroxyethyl]-1-methyl-3-(4-methylaminocarbonylphenyl)propylamine. The process for preparing the optically active R,S-phenethanolamines of the invention is provided as a further aspect of this invention, and is depicted by the following scheme:

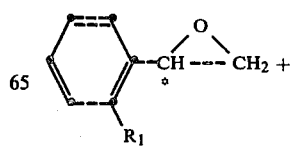

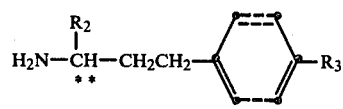

wherein R₁ and R₃ are as defined above, R₂ is methyl or ethyl, and C* is the R absolute stereochemical configuration and C** is the S absolute stereochemical configuration. Such condensation reactions normally are carried out in an unreactive organic solvent such as ethanol, dioxane, toluene, dimethylformamide or the like, and usually at a temperature of from about 50° to about 120° C. Under such conditions, the condensation generally is substantially complete after about 6 to about 10 hours, and the product phenethanolamine can be isolated by simply removing the reaction solvent, for instance by evaporation under reduced pressure. Further purification of the product thus formed can be accomplished if desired by standard methods including chromatography, crystallization, salt formation and the like.

As already pointed out, the optically active amines which are condensed with a styrene oxide are novel intermediate compounds and are accordingly provided by this invention. Such optically active amines can be prepared by reacting a ketone of the formula

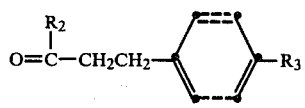

wherein R₂ is methyl or ethyl and R₃ is as defined above, with an optically active amine, for instance (−)-α-methylbenzylamine, to form the corresponding imine Schiff base. The reaction of the ketone and the optically active amine generally is carried out in an organic solvent such as benzene or toluene and in the presence of an acid catalyst such as p-toluenesulfonic acid. The imine which is formed is reduced, for instance by hydrogenation in the presence of a catalyst such as Raney nickel or the like. The reduced product, for example an optically active α-methylbenzylamine of the formula

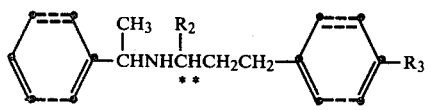

wherein R₂ is methyl or ethyl and R₃ is as defined above, can be purified by repeated crystallizations from a suitable organic solvent. Removal of the optically active α-methyl benzyl group by hydrogenolysis in the presence of palladium on charcoal then provides the optically active S-1-methyl(or ethyl)-3-(4-substituted phenyl)propylamine intermediates of the invention.

Another preferred method for preparing the phenethanolamine compounds of this invention comprises reacting an optically active mandelic acid with a phenylpropylamine to provide an amide, and then reducing the amide carbonyl to provide a compound of the invention. Such method is ideally suited to the preparation of compounds wherein R₃ is a hydroxy or alkoxycarbonyl substituent.

The reaction of a mandelic acid with a phenylpropylamine is best accomplished utilizing coupling reagents such as those commonly used in the synthesis of peptides. Such routinely used coupling reagents include carbodiimides such as N,N'-dicyclohexylcarbodiimide (DCC) and N,N'-diisopropylcarbodiimide, as well as N-ethoxycarbonyl-2-ethoxy-1,2-dihydroquinoline (EEDQ). Dicyclohexylcarbodiimide generally is a preferred coupling reagent. A substituted or unsubstituted 1-hydroxybenzotriazole can be employed to accelerate the reaction if desired. The general process for preparing peptides utilizing dicyclohexylcarbodiimide and 1-hydroxybenzotriazole is discussed in detail by Konig and Geiger in *Chem. Ber.*, 103, 788–798 (1970). According to such preferred process for preparing a compound of this invention, either R-2-phenyl-2-hydroxyacetic acid or R-2-(2-fluorophenyl)-2-hydroxyacetic acid is reacted with approximately an equimolar quantity of a 3-phenylpropylamine or an optically active S-1-alkyl-3-phenylpropylamine in the presence of a substantially equimolar amount of both dicyclohexylcarbodiimide and 1-hydroxybenzotriazole. The coupling reaction is best carried out in an organic solvent such as dimethylformamide, hexamethylphosphortriamide, acetonitrile, dichloromethane, and the like. The reaction normally is carried out at a reduced temperature, for example at a temperature below about 50° C., generally at about 0° to about 10° C. The reaction normally is substantially complete within about two to about twenty hours; however, longer reaction periods appear not to be detrimental to the desired product and can be utilized if desired.

The coupling of an acid and an amine in the presence of dicyclohexylcarbodiimide to form an amide converts the dicyclohexylcarbodiimide to dicyclohexylurea. This latter compound is characteristically quite insoluble in organic solvents and accordingly can be removed from the reaction mixture simply by filtration. Once the dicyclohexylurea is removed from the reaction mixture, the product amide can be isolated by removal of the reaction solvent, for instance by evaporation of the solvent under a reduced pressure. The product thus formed can be dissolved in a water immiscible organic solvent such as ethyl acetate and washed with aqueous sodium bicarbonate to remove any remaining 1-hydroxybenzotriazole. The amide so formed can, if desired, be further purified by routine procedures including crystallization and chromatography.

The amide next is reduced to provide the corresponding optically active N-phenylpropyl phenethanolamine comprehended by this invention. Reduction of such amide can be accomplished by any of a number of routine reduction processes, such as reaction with metal hydride reducing agents. A preferred reduction process comprises reaction of an amide with diborane. For example, an amide such as R,S-N-[2-(2-fluorophenyl)-2-hydroxy-1-oxoethyl]-1-ethyl-3-(4-hydroxyphenyl)-propylamine can be reacted with diborane to provide a phenethanolamine compound having the above formula. In such reduction reaction, the diborane typically is utilized in an excessive amount relative to the amide, such as from about 1 to about 4 molar excess. The reduction generally is carried out in an organic solvent such as tetrahydrofuran, diethyl ether, benzene, dichloromethane, toluene, dioxane, or like solvents. Such reduction reactions typically are complete within about two to twenty hours when carried out at a temperature of from about 0° to about 100° C. Any excess diborane and borane complex remaining in the reaction mixture after the reduction of the amide is complete can be decomposed by the addition to the reaction mixture of an alcohol such as methanol or ethanol and an acid such as hydrochloric acid. The reduced product thus formed can be isolated by simply removing the reaction solvent, for example by evaporation. The product, an optically active phenethanolamine having the above formula, generally exists as a solid and can thus be further purified by crystallization or chromatography. Alternatively, the amine so formed can be converted to an acid addition salt, as will be discussed more fully hereinbelow.

It should be recognized that the above-described processes for preparing a compound of the above formula can be carried out utilizing unresolved starting materials, thereby affording mixtures of racemic diastereomers of N-phenylpropyl phenethanolamines. Separation of the diastereomers so formed can be accomplished by normal processes when required. In those compounds having the above formula wherein $R_2$ is hydrogen, separation of the optical isomers at $\overset{*}{C}$ is not necessary. While the R-optical isomer of the phenethanol portion of compounds having the above formula (i.e., $\overset{*}{C}$) is required for useful biological activity, it is not a major disadvantage to have such R-isomer in admixture with the corresponding S-isomer (i.e. at $\overset{*}{C}$), since the S-isomer is substantially devoid of activity and causes no undesired side effects to a biological system at therapeutic doses. It therefore is convenient to prepare compounds wherein $R_2$ is hydrogen simply by reacting a phenylpropylamine with a dl-styrene oxide to provide a racemic mixture. Similarly, a dl-styrene oxide can be reacted with an optically active S-1-alkyl-3-phenylpropylamine to provide the corresponding R,S-phenethanolamine of this invention admixed with the corresponding S,S isomer. Such mixture can be utilized in the method of this invention without separation.

Use of the unresolved (at $\overset{*}{C}$) phenethanolamines of the above formula wherein $R_2^{*}$ is hydrogen may be particularly desirable economically if the compounds are to be utilized in the improvement of the quality of meat in livestock animals, such as cattle, sheep, and pigs. Such compounds function by removing, or preventing the formation of, excess adipose tissue in such animals. Such compounds accordingly have particular value in improving the quality of pig carcasses, an animal prone to being fat. In such use, the mixture of optical isomers, for example the R+S isomers of a compound having the formula

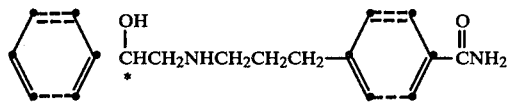

can be administered to a pig in an amount of from about 1.0 to about 25 mg/kg per day, normally as a feed additive. If desired, such dosage can be administered several times per day, for instance from 1 to about 4 or more times.

It should additionally be noted that separation of optical isomers at $\overset{*}{C}$ is required in the case of compounds of this invention wherein $R_2$ is methyl or ethyl. This invention comprehends only those phenethanolamine compounds of the above formula wherein the asymmetric center labelled $\overset{}{C}$ has the S absolute stereochemical configuration, since the R optical isomers (at the $\overset{}{C}$ asymmetric center) are potent inotropic agents and cannot be used to treat obesity without imparting a significant cardiac effect. The preparation and utility of certain of the R,R optical isomers of the above formula is fully described in the co-pending application of Mills, Schmiegel and Tuttle filed this even date herewith.

Another method for preparing compounds comprehended by this invention comprises reacting a phenethanolamine with an aldehyde or ketone to provide the corresponding Schiff base, followed by reduction of the Schiff base. Such process is illustrated by the following scheme:

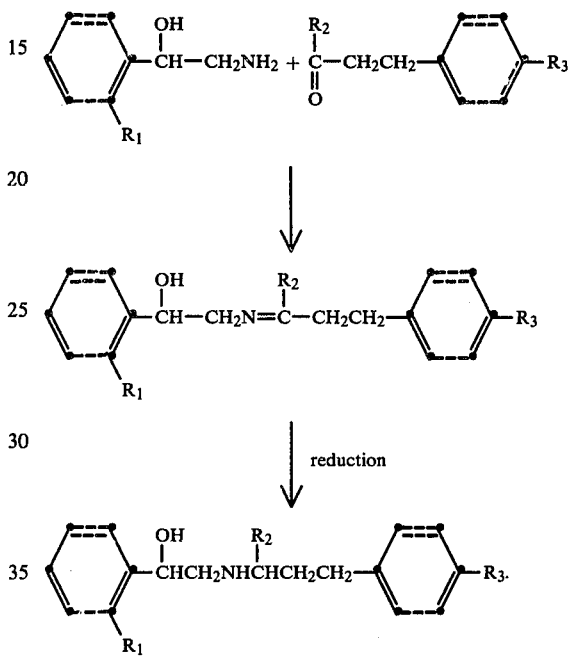

Ideally, optically active R-phenethanolamines are used in the reaction. For example, a compound such as R-2-phenyl-2-hydroxyethylamine can be condensed with about an equimolar quantity of a ketone such as methyl 2-(4-ethoxycarbonylphenyl)ethyl ketone. Such condensation of a phenethanolamine and a phenethyl ketone can be carried out in an organic solvent such as toluene, and generally in the presence of an acidic catalyst such as para-toluenesulfonic acid. The product from such condensation is an imine, i.e., a Schiff base, which upon reduction provides the corresponding phenethanolamine of the invention. Such reduction typically can be carried out by reaction with hydrogen or with a metal hydride such as sodium cyanoborohydride. The reduction of an imine wherein $R_2$ is methyl or ethyl generally affords a mixture of optical isomers at $\overset{**}{C}$, the separation of which can be accomplished utilizing standard techniques such as fractional crystallization.

Still another method for preparing the compounds of this invention comprises reacting a hydroxy protected 2-phenyl-2-hydroxyacetic acid acylating agent with a 3-phenylpropylamine or an optically active 1-alkyl-3-phenylpropylamine to provide an amide, and then reduction of the amide carbonyl group to provide a compound of this invention. Such process is depicted by the following scheme:

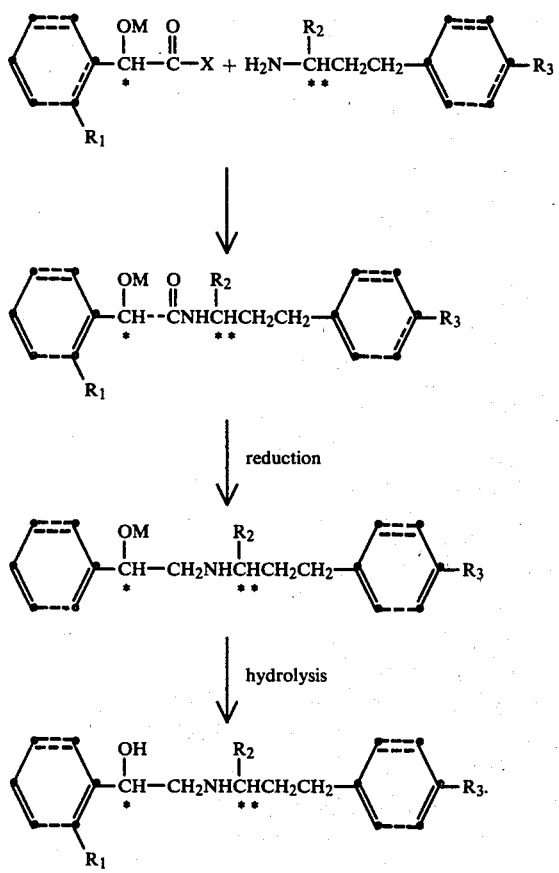

$R_1$, $R_2$ and $R_3$ in the above formulae are as defined above, X is a good leaving group and M is a readily removable hydroxy protecting group. Commonly used hydroxy protecting groups include acyl moieties such as acetyl, chloroacetyl and dichloroacetyl, as well as ether forming groups such as trimethylsilyl and the like. Such readily removable hydroxy protecting groups are more fully described by H. Haslam in *Protective Groups in Organic Chemistry*, J. F. W. McOmie, Ed., Plenum Press, New York, N.Y., 1973, Chapter 3. As noted above, X is defined as a good leaving group and includes halogen groups such as chloride and bromide, as well as acyloxy groups such as acetoxy and dichloroacetoxy. As an example of the preparation of a compound of this invention utilizing a hydroxy protected mandelic acid acylating agent, a compound such as R-2-(2-fluorophenyl)-2-hydroxyacetic acid can be reacted with dichloroacetyl chloride to provide R-2-(2-fluorophenyl)-2-dichloroacetoxyacetic acid. Reaction of this latter compound with a halogenating agent such as thionyl chloride or oxalyl chloride provides the corresponding acid chloride, namely R-2-(2-fluorophenyl)-2-dichloroacetoxyacetyl chloride. Reaction of such acid chloride with a phenylpropylamine, for instance S-1-methyl-3-(4-hydroxyphenyl)propylamine, provides the corresponding amide, which amide in the instant example would be R,S-N-[2-(2-fluorophenyl)-2-dichloroacetoxy-1-oxoethyl]-1-methyl-3-(4-hydroxyphenyl)propylamine. The amide so formed next is reduced, for example by reaction with diborane or the like, and the hydroxy protecting group is removed, for instance by hydrolysis, thus providing an optically active phenethanolamine having the above formula.

A further method for preparing compounds comprehended by this invention comprises reacting a phenacyl halide with a 3-phenylpropylamine or optically active S-1-alkyl-3-phenylpropylamine. For example, a phenacyl halide such as 2-fluorophenacyl bromide can be reacted with about an equimolar quantity of an amine such as S-1-methyl-3-(4-hydroxyphenyl)propylamine. Such alkylation reactions normally are carried out in a suitable solvent such as ethanol and in the presence of a base such as sodium carbonate or triethylamine. The reaction is complete within about six hours when carried out at about 50° C. and provides a ketone intermediate, for instance S-N-[2-(2-fluorophenyl)-2-oxoethyl]-1-methyl-3-(4-hydroxyphenyl)propylamine. The ketone thus formed can be isolated as the free amine base or as an acid addition salt. Reduction of such ketone, for example by reaction with sodium borohydride or the like, affords a compound of this invention, generally as a mixture of optical isomers at C. Such mixture of R, S and S,S optical isomers can be separated by standard procedures, or if desired can be utilized directly in the process of this invention, since the S,S isomer is essentially devoid of biological activity.

Compounds having the above formula wherein $R_3$ is hydroxyl, that is compounds of this invention which bear a phenolic hydroxyl group, can be readily acylated to provide compounds having the above formula in which $R_3$ is $C_1$–$C_4$ alkanoyloxy. As used herein, the term "$C_1$–$C_4$ alkanoyloxy" includes formyloxy, acetoxy, propionoxy, butyroxy, and isobutyroxy. The acylation of a compound of this invention having a phenolic hydroxyl group typically is accomplished by reacting the hydroxyl compound with an acylating agent such as a $C_1$–$C_4$ acid anhydride, or an acid halide such as an acid chloride or acid bromide. Typical acylating agents commonly employed include acetic anhydride, propionyl chloride, isobutyryl bromide, formic-acetic anhydride, and the like.

It may be desirable to protect the hydroxyl and amino groups of the phenethanolamine portion of the compound of this invention prior to acylation of a free phenolic hydroxyl group, thereby precluding any undesired side reactions. For example, a compound of this invention such as R,S-N-[2-(2-fluorophenyl)-2-hydroxyethyl]-1-ethyl-3-(4-hydroxyphenyl)propylamine can be reacted with thionyl chloride in the presence of a base such as triethylamine and in a solvent such as tetrahydrofuran to form a cyclic oxathiazole, thus effectively protecting both the hydroxyl group and the amino group of the phenethanolamine portion of the molecule. Such reaction converts the above-named compound into R,S-N-[1-ethyl-3-(4-hydroxyphenyl)propyl]-5-(2-fluorophenyl)-1-oxo-4,5-dihydro-1,2,3-oxathiazole. This latter compound can then be acylated at the free phenolic hydroxyl functionality without risk of affecting other sites in the molecule. For instance, R,S-N-[1-ethyl-3-(4-hydroxyphenyl)propyl]-5-(2-fluorophenyl)-1-oxo-4,5-dihydro-1,2,3-oxathiazole can be reacted with an acylating agent such as acetic anhydride or acetyl chloride in a solvent such as benzene, xylene, toluene, or the like, and in the presence of a base such as triethylamine, generally at a temperature of about 50° to 100° C., thus effecting acylation of the phenolic hydroxyl group to provide, in the instant case, R,S-N-[1-ethyl-3-(4-acetoxyphenyl)propyl]-5-(2-fluorophenyl)-1-oxo-4,5-dihydro-1,2,3-oxathiazole. The oxathiazole thus prepared is treated with an acid such as a dilute mineral acid in order to remove the protecting groups to thus recover the desired phenethanolamine. For example, the above-named oxathiazole can be treated with 1 N hydrochloric acid at a temperature of about 30° C. to provide R,S-N-[2-(2-fluorophenyl)-2-hydroxyethyl]-1-ethyl-3-(4-acetoxyphenyl)propylamine as the acid addition salt, which upon treatment with a base such as sodium carbonate affords the phenethanolamine of this invention as a free amine.

Compounds of the above formula wherein $R_3$ is aminocarbonyl can be prepared either directly, for example by reacting the appropriate substituted phenylpropylamine with a styrene oxide, or alternatively they can be derived from those compounds wherein $R_3$ is $C_1$-$C_2$ alkoxycarbonyl such as methoxycarbonyl or ethoxycarbonyl. For example, R-mandelic acid can be coupled with S-1-methyl-3-(4-methoxycarbonylphenyl)propylamine to provide, after reduction of the amide carbonyl, the corresponding phenethanolamine of this invention, namely R,S-N-(2-phenyl-2-hydroxyethyl)-1-methyl-3-(4-methoxycarbonylphenyl)propylamine. Such amine can be reacted with hydrazide for about 2 to 40 hours at about 50° to 100° C. to convert the alkoxycarbonyl group to a hydrazino carbonyl group. The latter compound is converted by hydrogenation to the corresponding aminocarbonyl derivative. Such hydrogenation is accomplished utilizing common catalysts such as Raney nickel or the like.

Phenethanolamines having the above formula wherein $R_3$ is methylaminocarbonyl preferably are prepared by reacting a styrene oxide with a 3-(4-methylaminocarbonylphenyl)propylamine. The required phenylpropylamine starting material can be prepared by simply reacting methylamine with the appropriate benzoyl chloride derivative. For example, S-1-ethyl-3-(4-chlorocarbonylphenyl)propylamine can be reacted with methylamine to provide S-1-ethyl-3-(4-methylaminocarbonylphenyl)propylamine. Reaction of the latter compound with a styrene oxide affords a compound of this invention.

The phenethanolamines provided by this invention are amines and as such are basic in nature. Consequently, they can readily be converted to acid addition salts by reaction with organic or inorganic acids. Accordingly, an additional embodiment of this invention comprises the non-toxic pharmaceutically acceptable salts of the N-phenylpropyl phenethanolamines of the above formula. The particular acids utilized to form salts of this invention are not critical, and such salts include those which are prepared by reaction of the amine of this invention with any of a number of common acids such as hydrochloric, hydrobromic, sulfuric, phosphoric, nitric, perchloric, formic, acetic, butyric, citric, maleic, succinic, oxalic, fumaric, lactic, methanesulfonic, p-toluenesulfonic, and related acids. The non-toxic pharmaceutically acceptable acid addition salts which are formed by reaction of an amine of this invention with an acid such as one of the above-named acids typically exist as highly crystalline solids, and thus lend themselves to ready purification by recrystallization from common solvents such as methanol, ethanol, ethyl acetate and the like. Additionally, such salts are easily formulated for convenient administration, particularly by the oral route, to subjects in need of treatment for obesity. When desired, such acid addition salts are readily converted to the corresponding free amine base by reaction with a suitable basic compound, for instance sodium or potassium hydroxide, sodium carbonate, triethylamine, sodium bicarbonate, and the like.

The following list of compounds is provided to illustrate the range of compounds comprehended by this invention. The representative listing is not intended to be inclusive of every compound claimed herein, but rather simply illustrates certain preferred compounds and the relative scope of the disclosure.

R,S-N-(2-phenyl-2-hydroxyethyl)-1-methyl-3-(4-hydroxyphenyl)propylamine;
R,S-N-(2-phenyl-2-hydroxyethyl)-1-methyl-3-(4-aminocarbonylphenyl)propylamine;
R,S-N-(2-phenyl-2-hydroxyethyl)-1-ethyl-3-(4-hydroxyphenyl)propylamine;
R,S-N-(2-phenyl-2-hydroxyethyl)-1-ethyl-3-(4-aminocarbonylphenyl)propylamine;
R,S-N-(2-phenyl-2-hydroxyethyl)-1-methyl-3-(4-methylaminocarbonylphenyl)propylamine;
R,S-N-(2-phenyl-2-hydroxyethyl)-1-methyl-3-(4-acetoxyphenyl)propylamine;
R,S-N-[2-(2-fluorophenyl)-2-hydroxyethyl]-1-methyl-3-(4-ethoxycarbonylphenyl)propylamine;
R,S-N-[2-(2-fluorophenyl)-2-hydroxyethyl]-1-ethyl-3-(4-methoxycarbonylphenyl)propylamine;
R-N-(2-phenyl-2-hydroxyethyl)-3-(4-methylaminocarbonylphenyl)propylamine;
R,S-N-(2-phenyl-2-hydroxyethyl)-1-methyl-3-(4-isobutyroxyphenyl)propylamine;
R,S-N-(2-phenyl-2-hydroxyethyl)-1-ethyl-3-(4-methylaminocarbonylphenyl)propylamine;
R-N-[2-(2-fluorophenyl)-2-hydroxyethyl]-3-(4-ethoxycarbonylphenyl)propylamine;
R,S-N-(2-phenyl-2-hydroxyethyl)-1-methyl-3-(4-ethoxycarbonylphenyl)propylamine;
R-N-(2-phenyl-2-hydroxyethyl)-3-(4-aminocarbonylphenyl)propylamine;
R,S-N-(2-phenyl-2-hydroxyethyl)-1-methyl-3-(4-hydroxyphenyl)propylaminium chloride;
R,S-N-(2-phenyl-2-hydroxyethyl)-1-methyl-3-(4-methylaminocarbonylphenyl)propylaminium bromide;
R,S-N-(2-phenyl-2-hydroxyethyl)-1-methyl-3-(4-hydroxyphenyl)propylaminium acetate;
R,S-N-(2-phenyl-2-hydroxyethyl)-1-methyl-3-(4-hydroxyphenyl)propylaminium butyrate;
R,S-N-(2-phenyl-2-hydroxyethyl)-1-methyl-3-(4-aminocarbonylphenyl)propylaminium succinate;

Obesity is a very serious disease that currently is the subject of a great deal of concern, particularly since no truly effective treatments are known. A full discussion of nutritional diseases and obesity in general is presented by Albrink in *Textbook of Medicine*, 12th Ed., 1969, W. B. Saunders Company, Philadelphia, Pa., pp. 1164–1174 and by Salans in *Current Therapy*, 1977, W. B. Saunders Company, pp. 455–460. The phenethanolamines provided by this invention are particularly useful due to their ability to effect an actual reduction in weight when administered to a mature obese animal. Such weight reduction is accomplished without a concomitant reduction in daily food consumption. When the compounds of this invention are administered to immature obese animals, the degree of weight gain is significantly reduced compared to that observed in young obese animals not receiving a compound of the invention.

The anti-obesity activity of the compounds of this invention has been demonstrated in a number of biological tests utilizing mice, rats and dogs. One of the major actions of the claimed compounds on a biological system appears to be the mobilization of fatty acids from adipose tissue stores. In a test designed to demonstrate such mobilization, a compound of this invention was administered to a total of eight normal fed rats of the Charles River strain, each weighing about 180 to 200 grams. A blood sample from each animal was taken immediately preceding the administration of the test compound and served as the control for each of the eight animals. A compound of this invention was then administered to each animal subcutaneously at the dose of 10 mg./kg. of body weight. Blood samples were then taken from each animal at intervals of 30, 60, 90 and 120 minutes after dosing, and the serum free fatty acid levels were determined for each blood sample. Table I presents the results of such test carried out with two compounds of this invention. The results demonstrate that a dramatic increase in serum free fatty acid levels is caused by a compound of this invention.

TABLE I

| | Average % of serum free fatty acid rise after dosing |
|---|---|
| R,S—N—(2-phenyl-2-hydroxy)-1-methyl-3-(4-hydroxyphenyl)-propylamine | 425% |
| R,S—N—(2-phenyl-2-hydroxyethyl)-1-methyl-3-(4-aminocarbonyl-phenyl)propylamine | 350% |

In a test designed to demonstrate the actual weight reducing effects of the compounds of this invention, viable yellow genetically obese mice were selected as a model. All of the animals were 6.5 months old at the beginning of the study. The animals were fed Purina Laboratory Chow and water ad libitum throughout the study. Five obese animals were randomly selected to receive 10 mg./kg. of R,S-N-(2-phenyl-2-hydroxyethyl)-1-methyl-3-(4-hydroxyphenyl)propylamine subcutaneously twice daily, and five animals received placebo. The initial body weight of each animal was determined on day 1 of the study prior to the first injections. Table II presents the results of the study. The data is presented as the average body weight in grams of the control group and of the group receiving the test compound. Such average body weight in grams is presented in column I under each of the indicated days. Column II under each of the indicated days provides the average food consumption in grams for the control group and for the test group.

The results presented in Table II demonstrate that the compounds of this invention cause an actual reduction in body weight in mature obese animals without causing a decrease in food consumption.

TABLE II

| | Day 1 | | Day 10 | | Day 20 | | Day 30 | | Day 40 | | Day 50 | |
|---|---|---|---|---|---|---|---|---|---|---|---|---|
| | I | II | I | II | I | II | I | II | I | II | I | II |
| Control group receiving placebo | 50 | 3.2 | 50 | 4.8 | 51 | 5.1 | 50 | 5.0 | 50 | 4.0 | 51 | 4.0 |
| test group receiving drug | 48 | 3.0 | 43 | 4.8 | 40 | 5.0 | 37 | 5.0 | 36.5 | 4.4 | 37 | 4.5 |

A similar study was carried out utilizing genetically obese Zucker rats. The phenethanolamines of the invention effected a dramatic weight reduction without decreasing daily food consumption when administered to adult obese rats (6 months and older). When administered to immature obese rats ranging in age from 2 to 5 months, the compounds were effective in preventing the excessive gain in weight as was observed with the young obese rats which did not receive a compound of this invention. Table III presents the results of a study carried out by administering R,S-N-(2-phenyl-2-hydroxyethyl)-1-methyl-3-(4-hydroxyphenyl)propylamine at 10 mg./kg. twice daily to the test animals. All animals were permitted to eat all the food and drink all the water they wanted. The food consumption of the animals given a compound of the invention did not differ significantly from the control animals receiving placebo. Each of the body weights reported in the table is the average weights of *five* animals in each of the test classes.

TABLE III

| | Day 1 body weight in grams | Day 20 body weight in grams | Day 40 body weight in grams | Day 60 body weight in grams | Day 80 body weight in grams |
|---|---|---|---|---|---|
| Immature Zucker controls | 490 | 500 | 525 | 550 | 570 |
| Immature Zucker rats receiving drug | 475 | 480 | 482 | 478 | 485 |
| Mature Zucker controls | 629 | 631 | 630 | 625 | 629 |
| Mature Zucker rats receiving drugs | 632 | 625 | 595 | 575 | 560 |

The anti-obesity drugs provided by this invention additionally have demonstrated their ability to effect weight reductions in obese dogs. Obese breeder beagles from the Pin Oak colony ranging in age from 4 to 9 years and weighing from 15.4 to 29.0 kg. were selected from the test. The dogs were fed ad libitum a Eucanuba diet containing sixteen percent fat for six months prior to the initiation of the study, thereby stabilizing the dogs' obesity. In one test, the animals received R,S-N-(2-phenyl-2-hydroxyethyl)-1-methyl-3-(4-hydroxyphenyl)propylaminium chloride at a subcutaneous dose of 3.2 mg./kg. twice each day. The effect of the drug on body weight was determined by measuring body weight in kilograms. No decrease in food consumption was noted. The results of five weeks treatment are summarized in Table IV.

TABLE IV

| | Weight in Kg. Day 1 | Weight in Kg. Day 35 | Weight loss Kg. | percent weight loss |
|---|---|---|---|---|
| Dog 1 | 17.2 | 15.8 | 1.4 | 8% |
| Dog 2 | 29.2 | 25.5 | 3.7 | 12.5% |
| Dog 3 | 18.7 | 16.5 | 2.2 | 12% |
| Dog 4 | 16.2 | 15.0 | 1.2 | 7.5% |

In a similar test utilizing mature obese beagle hounds, fed ad libitum on standard dog chow, R,S-N-(2-phenyl-2-hydroxyethyl)-1-methyl-3-(4-aminocarbonylphenyl)-propylaminium chloride was administered orally at 15 mg./kg. twice daily for twenty-seven days. The effect of the drug on body weight was determined by measuring body weight in kilograms and girth size in inches. Two dogs were selected as control animals receiving food and water ad libitum, but no drug. Table V presents the results of the test. As the data demonstrates, the control dogs did not fluctuate a great deal in weight or girth size. In contrast, the obese dogs treated with a compound of this invention lost from 1.8 to 2.9 kilograms during a 27 day treatment period, and the girth of such obese dogs decreased by as much as 2 inches in the same period of time.

TABLE V

|  | Day 1 | | Day 7 | | Day 14 | | Day 21 | | Day 27 | |
| --- | --- | --- | --- | --- | --- | --- | --- | --- | --- | --- |
|  | Weight kg. | girth size inches | Weight kg. | girth size inches | Weight kg. | girth size inches | Weight kg. | girth size inches | Weight kg. | girth size inches |
| Control animal | 16.7 | 24 | 16.2 | 24.5 | 16.9 | 24.5 | 16.2 | 25 | 16.4 | 25 |
| Control animal | 16.3 | 25 | 16.4 | 25 | 16.5 | 24 | 16.5 | 24 | 16.5 | 25 |
| Test animal | 20.4 | 27.5 | 20.5 | 27 | 19.6 | 27 | 18.1 | 27 | 17.5 | 25.5 |
| Test animal | 17.7 | 26 | 16.9 | 26 | 16.7 | 25.5 | 15.9 | 26 | 15.9 | 25 |
| Test animal | 20.7 | 26 | 20.0 | 26 | 19.7 | 25.5 | 19.8 | 25 | 18.6 | 25 |

As already pointed out, the unique physiological effect of the compounds of this invention is their potent anti-obesity activity and their physiologically tolerable degree of cardiovascular activity. In contrast to the R,S-compounds of this invention, the R,R-optical isomers hereinabove referred to are strongly inotropic. This unique and unexpected separation of biological activity is achieved by separating the optical isomers of certain phenethanolamines, and by simply selecting the proper chemical compounds in those instances where the phenethanolamines have only a single asymmetric center.

The unique separation of the physiological activity of the R,S-isomers of this invention compared to the inotropically active R,R-optical isomers has been demonstrated in dogs. The compounds to be evaluated were administered intravenously to dogs having implanted cardiovascular transducers for measurement of the derivative of the left ventricular pressure, which is the index of cardiac contractile force. A dose of compound sufficient to cause a twenty-five percent increase in contractile force was administered. The dose required to effect such increase in contractile force is reported in Table VI as the $ED_{25}$ in mcg./kg. The results demonstrate that very little of the inotropically active R,R-isomers is required to effect a twenty-five percent increase in contractile force, whereas a significantly larger dose of the corresponding R,S-isomer is required to cause the same effect.

TABLE VI

| Compound administered | Contractile Force $ED_{25}$ mcg./kg. |
| --- | --- |
| R,S—N—(2-phenyl-2-hydroxyethyl)-1-methyl-3-(4-hydroxyphenyl)-propylamine | 100.0 |
| R,R—N—(2-phenyl-2-hydroxyethyl)-1-methyl-3-(4-hydroxyphenyl)-propylamine | 2.5 |
| R,S—N—(2-phenyl-2-hydroxyethyl)-1-methyl-3-(4-aminocarbonylphenyl)-propylamine | 100.0 |
| R,R—N—(2-phenyl-2-hydroxyethyl)-1-methyl-3-(4-aminocarbonylphenyl)-propylamine | 3.0 |

Because of the surprisingly low inotropic activity of the phenethanolamines of this invention, they can be administered to an animal at doses large enough to effect release of free fatty acids from adipose stores without causing a substantial increase in the pumping force of the heart. Such unique biological spectrum of the compounds of this invention renders them particularly useful in the control of weight in obese animals. As used herein, "weight control in obese animals" refers to the ability of the compounds of this invention to effect an actual weight reduction when administered to a mature obese animal, whereas such compounds are effective in the prevention of excessive weight gain when administered to immature obese animals. The terms "mature" and "immature" are used herein to refer to the generally accepted definitions of age and growth patterns. "Obesity" is an art recognized term and is used as such herein.

An additional aspect of this invention is a method for controlling weight in obese animals. While the anti-obesity effective dose of a compound of this invention employed in the control of obesity will vary depending on the particular drug employed and the severity of the condition being treated, the usual dosage of a compound of this invention will be from about 1.0 to about 25 mg. per kilogram of animal body weight. The compounds of the invention preferably will be administered orally at a dosage of from about 1 to about 5 mg./kg., generally given in individual doses from one to four times per day. When desired, the drug can be administered orally in the form of a tablet or capsule, or alternatively in sustained release form. According to the method of this invention a compound defined by the above general formula is administered to a mature obese animal to effect an actual reduction in weight without diminishing the daily food consumption. The drug will be administered daily, at increasing dosage levels if desired, until the desired weight reduction is effected. The compounds of the invention can be administered to an immature obese animal to effect a reduction in weight gain without a diminished daily food consumption. Once the immature obese animal reaches maturity, a reduction of weight will be effected until a substantially normal weight is achieved.

The phenethanolamines comprehended by this invention can be formulated by normal procedures for convenient administration by any of a number of routes. It is preferred that the compounds be formulated for oral administration. Pharmaceutical formulations which are useful in weight control in obese animals are provided in a further embodiment of this invention.

Such pharmaceutical compositions can contain, as active ingredient, one or more of the compounds provided by this invention, in combination if desired with any of the inactive isomers as hereinbefore indicated, in addition to any of a number of pharmaceutically acceptable carriers or diluents. Typical carriers and diluents commonly used include gelatin, starch, dextrose, sucrose, lactose, cellulose derivatives, stearates, polyvinylpyrrolidine, glycerine, ethyl lactate, sorbitol, mannitol, and the like. A suitable pharmaceutical composition can additionally include any of a number of common preserving agents, stabilizers, antioxidants, taste correctors, and the like. Examples of such additives include ascorbic acid, sorbic acid, various esters of p-hydroxybenzoic acid, and the like.

Typical pharmaceutical compositions useful in the treatment of obesity according to this invention will generally include from about 1 to about 50 percent by weight of a compound of this invention as active ingredient. The remainder of said pharmaceutical composition will comprise suitable carriers and diluents, and any of the indicated inactive optical isomers as desired.

A pharmaceutical composition containing as active ingredient at least one of the compounds of this invention can be molded into tablets, encapsulated into empty gelatin capsules, or made into a solution or suspension. Such pharmaceutical compositions can be administered to an obese subject in need of treatment by any of a number of routes, including the oral and parenteral routes. A preferred formulation, for example, comprises about 250 mg. of R,S-N-(2-phenyl-2-hydroxyethyl)-1-methyl-3-(4-aminocarbonylphenyl)propylaminium chloride admixed with any of a number of suitable carriers and molded into a tablet for oral administration to an obese human subject at the rate of from 1 to about 4 tablets per day for effective weight control.

In an effort to more fully illustrate particular aspects of this invention, the following detailed examples of the preparation of starting materials and the final products of this invention are provided. The examples are representative only and should not be construed as limiting in any respect.

EXAMPLE 1

Preparation of R-styrene oxide

To a cold stirred solution of 300 g. of R-mandelic acid in 2000 ml. of tetrahydrofuran was added dropwise over two hours 3000 ml. of a 1 molar solution of diborane in tetrahydrofuran. The reaction mixture was stirred for twelve hours at 25° C. following complete addition, and then was cooled to 0° C. in an ice water bath. To the cold solution was added 600 ml. of methanol dropwise over thirty minutes, and the reaction mixture was then stirred for another three hours. Removal of the solvent by evaporation under reduced pressure provided 260 g. of the product as a solid. The solid was crystallized from diethyl ether to provide R-2-phenyl-2-hydroxyethanol.

A solution of 256.7 g. of R-2-phenyl-2-hydroxyethanol in 1000 ml. of toluene containing 50 ml. of pyridine was stirred at 0° C. while a solution of 372.1 g. of p-toluenesulfonyl chloride in 400 ml. of toluene was added dropwise over two hours. The reaction mixture was stirred at 0° C. for forty-eight hours and then filtered to remove the precipitated pyridine hydrochloride. The filtrate was concentrated to dryness by evaporation under reduced pressure to provide the product as an oil. The oil was dissolved in fresh toluene, washed with dilute hydrochloric acid and with water, and dried. Evaporation of the solvent under reduced pressure and crystallization of the product from diethyl ether and hexane afforded 435 g. of R-2-phenyl-2-hydroxy-1-p-toluenesulfonyloxyethane. The product thus formed was dissolved in 1000 ml. of dimethyl sulfoxide containing 418 ml. of 5 N sodium hydroxide. The alkaline solution was stirred at 0° C. for twelve hours, and then was poured into ice water. The product was extracted into 50% diethyl ether-pentane, and the organic layer was separated, washed with water and dried. Removal of the solvent by evaporation afforded, after distillation, 165 g. of R-styrene oxide, B.P. 55°–56° C. 0.6 torr. $[\alpha]_D$ −23.7° (chloroform).

EXAMPLE 2

Preparation of R-ortho-fluorostyrene oxide

One hundred three grams of dl-o-fluoromandelic acid was resolved by reaction with d(+)-α-methylbenzylamine to form the racemic salt, and crystallization of the salt from ethanol and ethyl acetate to provide optically active α-methylbenzylammonium 2-(2-fluorophenyl-2-hydroxy)acetate, M.P. 155°–157° C. $[\alpha]_D$ −43.1° (MeOH). The salt thus formed was hydrolyzed to the free acid to provide R-ortho-fluoromandelic acid, M.P. 88°–90° C. $[\alpha]_D$ −138° (MeOH). The acid was then converted to R-ortho-fluorostyrene oxide by the procedure of Example 1, B.P. 58°–61° C. (3 torr), $[\alpha]_D$ −32.7° (chloroform).

EXAMPLE 3

Preparation of
S-1-methyl-3-(4-aminocarbonylphenyl)propylamine

The oil from 280 g. of a 50% dispersion of sodium hydride in mineral oil was removed by several washings with hexane. The hexane was replaced with 1.5 l. of dimethylformamide, and the mixture was stirred and cooled in an ice-bath while 950 g. of ethyl acetoacetate was slowly added. After the sodium hydride had reacted a solution of 314 g. of α-bromo-p-toluic acid in 500 ml. of dimethylformamide was added. The ice bath was removed and the mixture was allowed to stir at 25° C. for eighteen hours, poured into water acidified with 3 N hydrochloric acid and extracted with ethyl acetate. The combined organic layers were washed with water and brine and dried over anhydrous sodium sulfate. The solvent and excess ethyl acetoacetate was removed at reduced pressure to afford 500 g. of oil.

The crude oil was combined with 1.2 l. of glacial acetic acid, 140 ml. of concentrated hydrochloric acid and 750 ml. of water and heated at refluxed for three and one half hours. The solvents were removed under reduced pressure and the residue was dissolved in a mixture of ether and xylene and washed with water. The solid obtained after removal of the solvents was recrystallized twice from a mixture of ethanol and water to give 111 g. of 4-(4-carboxyphenyl)-2-butanone, m.p. 120.5°–123° C.

Analysis calc. for $C_{11}H_{12}O_3$; Theory: C, 68.74; H, 6.29. Found: C, 68.99; H, 6.10.

A mixture of 9.50 g. of 4-(4-carboxyphenyl)-2-butanone, 100 ml. of benzene, 15.7 g. of oxalyl chloride and one drop of dimethylformamide was stirred and warmed to 50° C. for two hours. The reaction mixture was then allowed to stir for eighteen hours at 25° C. and concentrated under reduced pressure. The residue was dissolved in 50 ml. of dioxane and, with stirring, was added slowly to 300 ml. of cold (0° C.) concentrated ammonium hydroxide. The mixture was stirred for seventy-five minutes and diluted to 1 l. with water. The solid was removed by filtration, washed with water, dried and recrystallized from a mixture of methanol and ether to provide 4.1 g. of 4-(4-aminocarbonylphenyl)-2-butanone, m.p. 144°–146° C. An analytical sample, m.p. 149°–150° C., was obtained by recrystallizing twice from a mixture of methanol and ether.

Analysis calc. for $C_{11}H_{13}NO_2$; Theory: C, 69.09; H, 6.85; N, 7.32. Found: C, 68.98; H, 7.10, N, 6.99.

A solution of 45.7 g. of methyl 2-(4-aminocarbonylphenyl)ethyl ketone in 400 ml. of toluene containing 29.0 g. of (—)-α-methylbenzylamine and 1.0 g. of p-toluenesulfonic acid was heated at reflux for four hours with removal of water via a Dean Stark trap. After cooling the reaction mixture to room temperature, the solvent was removed therefrom by evaporation under reduced pressure to provide S-N-(α-methylbenzyl)-1-methyl-3-(4-aminocarbonylphenyl)propylimine. The imine was hydrogenated in 625 ml. of methanol utilizing 15 g. of Raney Nickel as the catalyst to provide a mixture of optical isomers of N-(α-methylbenzyl)-1-methyl-3-(4-aminocarbonylphenyl)propylamine. The amine was reacted with hydrogen chloride to provide the corresponding acid addition salt as a solid. The mixture was purified by repeated crystallization of the salt from methanol and acetonitrile to provide 23.6 g. of optically active S,S-N-(α-methylbenzyl)-1-methyl-3-(4-aminocarbonylphenyl)propylaminium chloride. M.P. 256°–258° C. $[\alpha]_D$ —80.1° (MeOH).

A solution of 16.3 g. of the salt in 480 ml. of ethanol containing 3.0 g. of five percent palladium suspended on carbon was hydrogenated for twenty-two hours at 50° C. under a pressure of 60 p.s.i. The reaction mixture then was filtered and the solvent was removed from the filtrate by evaporation under reduced pressure to provide the product as a solid. The solid was recrystallized three times from ethanol and ethyl acetate to afford 9.4 g. of S-1-methyl-3-(4-aminocarbonylphenyl)propylaminium chloride. M.P. 237°–240° C. $[\alpha]_D$ —8.2 (MeOH).

Analysis calc. for $C_{11}H_{17}ClN_2O$; Theory: C, 57.76; H, 7.49; N, 12.25 Found: C, 57.65; H, 7.57; N, 12.10

EXAMPLE 4

Preparation of
S-1-methyl-3-(4-methylaminocarbonylphenyl)propylamine

Optically active S,S-N-(α-methylbenzyl)-1-methyl-3-(4-methoxycarbonylphenyl)propylamine was hydrolyzed by reaction with 10 percent aqueous hydrochloric acid to provide optically active S,S-N-(α-methylbenzyl)-1-methyl-3-(4-hydroxycarbonylphenyl)propylaminium chloride. M.P. 234°–237° C. The acid thus formed was reacted with oxalyl chloride in benzene to provide the corresponding optically active acid chloride. The acid chloride was dissolved in dioxane and added dropwise to a stirred solution of methylamine in 50 ml. of dioxane. The reaction mixture was stirred for twelve hours at room temperature, and then diluted with 100 ml. of water. The aqueous reaction mixture was extracted with ethyl acetate, and the organic layer was separated, washed with water and dried. The solvent was removed by evaporation under reduced pressure to provide, after chromatography over silica gel, optically active S,S-N-(α-methylbenzyl)-1-methyl-3-(4-methylaminocarbonylphenyl)propylamine. Hydrogenation of the product thus formed according to the procedure of Example 3 effected de-benzylation to provide S-1-methyl-3-(4-methylaminocarbonylphenyl)propylaminium chloride. $[\alpha]_D$ —6° $[\alpha]_{365}$ —42.3° (MeOH).

The following optically active S-1-methyl(or ethyl)-3-(4-substituted phenyl)propylamines are prepared by the method of Examples 3 and 4.

S-1-methyl-3-(4-hydroxyphenyl)propylamine;
S-1-ethyl-3-(4-ethoxycarbonylphenyl)propylamine;
S-1-ethyl-3-(4-acetoxyphenyl)propylamine;
S-1-methyl-3-(4-methoxycarbonylphenyl)propylamine;
and the like.

EXAMPLE 5

R,S-N-(2-Phenyl-2-hydroxyethyl)-1-methyl-3-(4-methylaminocarbonylphenyl)propylamine To a refluxing solution of 3.6 g. of S-1-methyl-3-(4-methylaminocarbonylphenyl)propylamine in 50 ml. of ethanol was added dropwise over ten minutes a solution of 2.1 g. of R-styrene oxide in 20 ml. of ethanol. Following complete addition of the styrene oxide, the reaction mixture was heated at reflux for four hours and then cooled to 25° C. and stirred at that temperature for twelve hours. The solvent was next removed by evaporation under reduced pressure to provide an oil which was then crystallized from diethyl ether to provide 3.5 g. of the product as a solid. The solid was recrystallized from ethyl acetate and diethyl ether to afford 1.7 g. of R,S-N-(2-phenyl-2-hydroxyethyl)-1-methyl-3-(4-methylaminocarbonylphenyl)propylamine. M.P. 158°–160° C.

The amine so formed was converted to the hydrochloride salt by reaction with hydrogen chloride in diethyl ether to provide, following crystallization from methanol and ethyl acetate, 1.2 g. of R,S-N-(2-phenyl-2-hydroxyethyl)-1-methyl-3-(4-methylaminocarbonylphenyl)propylaminium chloride. M.P. 179°–182° C.

Analysis calc. for $C_{20}H_{27}ClN_2O_2$; Theory: C, 66.19; H, 7.50; N, 7.72. Found: C, 66.40; H, 7.82; N, 7.49.

EXAMPLE 6

R,S-N-(2-Phenyl-2-hydroxyethyl)-1-ethyl-3-(4-hydroxyphenyl)propylamine

A solution of 7.16 g. of S-1-ethyl-3-(4-hydroxyphenyl)propylamine in 50 ml. of N,N-dimethylformamide (DMF) was cooled in an ice-water bath and stirred under a nitrogen gas atmosphere while a solution of 6.08 g. of R-mandelic acid and 5.41 g. of 1-hydroxybenzotriazole in 15 ml. of DMF was added in one portion. A solution of 8.24 g. of dicyclohexylcarbodiimide in 10 ml. of DMF was added dropwise over thirty minutes to the stirred reaction mixture. The reaction mixture was stirred for two hours at 5° C., and then allowed to set for twelve hours at 0° C. Dicyclohexylurea had precipitated out of solution, and was separated from the reaction mixture by filtration. Removal of the solvent from the filtrate by evaporation under reduced pressure provided a solid residue. The solid was purified by washing it with sodium carbonate followed by crystalization from acetonitrile to provide 7.31 g. of R,S-N-(2-phenyl-2-hydroxy-1-oxoethyl)-1-ethyl-3-(4-hydroxyphenyl)propylamine. M.P. 116°–118.5° C. $[\alpha]_D$ —61° (MeOH).

Analysis calc. for $C_{19}H_{23}NO_3$; Theory: C, 72.82; H, 7.40; N, 4.47. Found: C, 72.73; H, 7.22; N, 4.77.

A solution of 6.17 g. of the amide thus formed in 70 ml. of tetrahydrofuran (THF) was added dropwise over one hour to a stirred solution of 60 ml. of 1 molar diborane in THF. Following the addition, the reaction mixture was stirred at 24° C. under a nitrogen gas atmosphere for forty-eight hours. Excess methanol then was added to the reaction mixture in order to decompose any unreacted diborane. The solvents were removed from the reaction mixture by evaporation under reduced pressure to provide the product as an oil. The oil so formed was dissolved in ethyl alcohol and diethyl ether, and excess hydrogen chloride gas was bubbled through the reaction mixture in order to form the hydrogen chloride acid addition salt. The salt precipitated out of solution and was removed therefrom by filtration. The solid product so formed was recrystallized several times from ethyl acetate to afford 171 mg. of R,S-N-(2-phenyl-2-hydroxyethyl)-1-ethyl-3-(4-hydroxyphenyl)propylaminium chloride. M.P. 148°–151° C. $[\alpha]_D$ −25.0° (MeOH).

Analysis calc. for $C_{19}H_{26}ClNO_2$; Theory: C, 67.92; H, 7.80; N, 4.17. Found: C, 67.97; H, 7.72; N, 4.45.

EXAMPLE 7

R,S-N-[2-(2-Fluorophenyl)-2-hydroxyethyl]-1-methyl-3-(4-hydroxyphenyl)propylamine A solution of 15.05 g. of S-1-methyl-3-(4-benzyloxyphenyl)propylamine in 50 ml. of DMF was cooled in an ice-water bath and stirred under a nitrogen gas atmosphere while a solution of 10.0 g. of R-2-(2-fluorophenyl-2-hydroxy)acetic acid and 7.97 g. of 1-hydroxybenzotriazole in 50 ml. of DMF was added in one portion. The reaction mixture was stirred at 5° C. while a solution of 12.15 g. of dicyclohexylcarbodiimide in 20 ml. of DMF was added dropwise over thirty minutes. The reaction mixture was stirred at 5° C. for one hour, and then allowed to stand at 9° C. for twelve hours. Dicyclohexylurea had precipitated out of solution, and was removed from the reaction mixture by filtration. The filtrate was diluted with ethyl acetate, washed with sodium carbonate, and then concentrated by evaporation of the solvent under reduced pressure, thus providing 23.0 g. of R,S-N-[2-(2-fluorophenyl)-2-hydroxy-1-oxoethyl]-1-methyl-3-(4-benzyloxyphenyl)propylamine as an oil.

To a stirred solution of 15.2 g. of lithium aluminum hydride in 800 ml. of diethyl ether was added dropwise over one hour a solution of 23.0 g. of the amide thus formed in 100 ml. of THF. After the addition was complete, the reaction mixture was heated at reflux for six hours, and then stirred for an additional twelve hours at 24° C. Any unreacted lithium aluminum hydride remaining in the reaction mixture was decomposed by the dropwise addition of 16 ml. of water, followed by the addition of 12 ml. of twenty percent aqueous sodium hydroxide solution and 56 ml. of water. Filtration and removal of the solvents from the reaction mixture by evaporation under reduced pressure provided R,S-N-[2-(2-fluorophenyl)-2-hydroxyethyl]-1-methyl-3-(4-benzyloxyphenyl)propylamine. The residue so formed was dissolved in ethyl alcohol and diethyl ether, and excess hydrogen chloride gas was bubbled through the solution. The precipitate which formed was collected by filtration and recrystallized twice from ethyl alcohol and diethyl ether, affording 10.0 g. of R,S-N-[2-(2-fluorophenyl)-2-hydroxyethyl]-1-methyl-3-(4-benzyloxyphenyl)propylaminium chloride. M.P. 162°–163° C.

Analysis calc. for $C_{25}H_{29}ClFNO_2$; Theory: C, 69.84; H, 6.80; N, 3.26. Found: C, 70.04; H, 6.95; N, 3.41.

A solution of 10.0 g. of the salt thus formed in 190 ml. of ethyl alcohol containing 2.0 g. of a suspension containing five percent of palladium on carbon was heated at 50° C. and stirred for two hours under a hydrogen gas atmosphere at 50 p.s.i. The reaction mixture then was cooled to room temperature and filtered. The filtrate was concentrated by evaporation of the solvent under reduced pressure, thus affording, after crystallization twice from ethanol and ether, 6.9 g. of R,S-N-[2-(2-fluorophenyl)-2-hydroxyethyl]-1-methyl-3-(4-hydroxyphenyl)propylaminium chloride. M.P. 180°–183° C. $[\alpha]_D$ −40.6° (MeOH).

Analysis calc. for $C_{18}H_{23}ClFNO_2$; Theory: C, 63.62; H, 6.82; Cl, 10.43; F, 5.54; N, 4.12. Found: C, 63.44; H, 6.81; Cl, 10.63; F, 5.38; N, 4.27.

EXAMPLE 8

R,S-N-[2-(2-Fluorophenyl)-2-hydroxyethyl]-1-ethyl-3-(4-hydroxyphenyl)propylamine A solution of 11.62 g. of S-1-ethyl-3-(4-hydroxyphenyl)propylamine in 50 ml. of DMF was cooled in an ice-water bath and stirred under a nitrogen gas atmosphere while to it was added in one portion a solution of 11.0 g. of R-2-(2-fluorophenyl-2-hydroxy)acetic acid in 20 ml. of DMF containing 8.78 g. of 1-hydroxybenzotriazole. The reaction mixture was stirred at 5° C. while a solution of 13.39 g. of dicyclohexylcarbodiimide in 15 ml. of DMF was added dropwise over thirty minutes. Following complete addition of the dicyclohexylcarbodiimide solution, the reaction mixture was stirred at 5° C. for two hours, and then was stored at 0° C. for an additional seventy-two hours. Dicyclohexylurea precipitated out of solution and was removed from the reaction mixture by filtration. The filtrate was concentrated by evaporation of the solvent under reduced pressure to provide an oil. The oil was dissolved in 200 ml. of ethyl acetate, and washed with dilute aqueous hydrochloric acid solution, with aqueous sodium carbonate solution, and with water. The solution was dried and the solvent was removed therefrom by evaporation under reduced pressure to provide R,S-N-[2-(2-fluorophenyl)-2-hydroxy-1-oxoethyl]-1-ethyl-3-(4-hydroxyphenyl)propylamine as a solid. M.P. 114°–118° C.

A solution of 13.0 g. of the above-named amide derivative in 100 ml. of tetrahydrofuran (THF) was added dropwise over one hour to a stirred solution of 105 ml. of 1 molar diborane in THF. Following complete addition of the amide derivative, the reaction mixture was stirred for six hours at 24° C., and then was cooled to 0° C. and allowed to set for twelve hours. The reaction mixture was next warmed to room temperature and stirred while excess methanol was added to decompose any unreacted diborane remaining in the reaction mixture. Evaporation of the reaction solvent under reduced pressure then provided R,S-N-[2-(2-fluorophenyl)-2-hydroxyethyl]-1-ethyl-3-(4-hydroxyphenyl)propylamine as an oil. The oil so formed was dissolved in ethanol, and diethyl ether containing excess hydrogen chloride gas was added. The hydrochloride salt of the above-named amine precipitated out of solution, and was recovered by filtration. Recrystallization of the solid so formed from ethanol and diethyl ether afforded R,S-N-[2-(2-fluorophenyl)-2-hydroxyethyl]-1-ethyl-3-(4-hydroxyphenyl)propylaminium chloride. M.P. 121°–124° C. $[\alpha]_D$ −27.3° (MeOH).

Analysis calc. for $C_{19}H_{25}ClFNO_2$; Theory: C, 64.49; H, 7.12; Cl, 10.02; F, 5.37; N, 3.96. Found: C, 64.58; H, 6.91; Cl, 10.16; F, 5.47; N, 4.11.

EXAMPLE 9

R,S-N-(2-Phenyl-2-hydroxyethyl)-1-methyl-3-(4-hydroxyphenyl)propylamine

A solution of 122.0 g. of S-1-methyl-3-(4-hydroxyphenyl)propylamine in 300 ml. of DMF was cooled to 5° C. in an ice-water bath and stirred while a solution of 112.6 g. of R-mandelic acid and 100.0 g. of 1-hydroxybenzotriazole in 300 ml. of DMF was added in one portion. The reaction mixture was stirred at 5° C. while a solution of 156.0 g. of dicyclohexylcarbodiimide in 500 ml. of DMF was added dropwise over two hours. Following the complete addition of the dicyclohexylcarbodiimide, the reaction mixture was stirred for an additional fifteen minutes, and then was allowed to set at 0° C. for twelve hours. The reaction mixture then was filtered to remove the precipitated dicyclohexylurea. Next, the solvent was removed from the reaction mixture by evaporation under reduced pressure, leaving an oily residue. The oil so formed was dissolved in 1000 ml. of ethyl acetate and washed with aqueous sodium carbonate and water. After drying the solution, the solvent was removed by evaporation under reduced pressure, thus providing 205.8 g. of R,S-N-(2-phenyl-2-hydroxy-1-oxoethyl)-1-methyl-3-(4-hydroxyphenyl)-propylamine. The amide thus formed was recrystallized from ethyl acetate and hexane. M.P. 219°-223° C. $[\alpha]_D$ −54.1° (MeOH).

Analysis calc. for $C_{18}H_{21}NO_3$; Theory: C, 72.22; H, 7.07; N, 4.68. Found: C, 71.98; H, 6.79; N, 4.89.

A solution of 168.2 g. of the amide and 170 ml. of triethylamine in 3000 ml. of benzene and 700 ml. of THF was stirred at 24° C. while 143 ml. of trimethylchlorosilane was added portionwise. The reaction mixture was stirred for thirty minutes and then filtered to remove the precipitated triethylamine hydrochloride. The filtrate was concentrated by evaporation of the solvent under reduced pressure, leaving an oily residue. The oil was next dissolved in 1000 ml. of THF, and the solution was stirred at 24° C. under a nitrogen gas atmosphere while 1300 ml. of 1 molar diborane in THF was added portionwise. The reaction mixture was stirred at room temperature for sixteen hours, and then excess methanol was added to the solution in order to decompose any unreacted diborane and to hydrolyze the trimethylsilyl ester. Removal of the solvent by evaporation under reduced pressure provided an oil. The oil was dissolved in diethyl ether containing hydrogen chloride, and the salt which formed was collected by filtration and recrystallized from ethanol and diethyl ether, affording 131.0 g. of R,S-N-(2-phenyl-2-hydroxyethyl)-1-methyl-3-(4-hydroxyphenyl)propylaminium chloride. M.P. 149°-150.5° C. $[\alpha]_D$ −51.7° (MeOH).

EXAMPLE 10

R,S-N-(2-Phenyl-2-hydroxyethyl)-1-methyl-3-(4-hydroxyphenyl)propylamine

A solution of 10.4 g. of S-1-methyl-3-(4-benzyloxyphenyl)propylamine in 150 ml. of DMF was stirred at room temperature under a nitrogen gas atmosphere while 6.35 g. of R-mandelic acid and 5.63 g. of 1-hydroxybenzotriazole were added. The reaction mixture was cooled to −5° C. in an ice and methanol bath and stirred while a solution of 9.03 g. of dicyclohexylcarbodiimide in 70 ml. of DMF was added dropwise over ten minutes. The reaction mixture then was stirred at 5° C. for one hour and then stored at 0° C. for twelve hours. The reaction mixture next was filtered, thus removing the precipitated dicyclohexylurea. The filtrate was concentrated by evaporation of the solvent under reduced pressure to provide an oily residue. The oil so formed was dissolved in 400 ml. of benzene and washed with aqueous sodium carbonate solution, with 1 N hydrochloric acid solution, and with water. After drying the reaction mixture, the solvent was removed by evaporation under reduced pressure, providing 13.6 g. of R,S-N-(2-phenyl-2-hydroxy-1-oxoethyl)-1-methyl-3-(4-benzyloxyphenyl)propylamine as a crystalline solid. M.P. 102°-104.5° C. $[\alpha]_D$ −48.98° (MeOH).

Analysis calc. for $C_{25}H_{27}NO_3$; Theory: C, 77.09; H, 6.99; N, 3.60. Found: C, 76.87; H, 7.03; N, 3.65.

A solution of 110 ml. of 1 molar diborane in THF was diluted with an additional 100 ml. of THF. The solution was cooled in an ice-acetone bath and stirred under a nitrogen gas atmosphere while a solution of 12.3 g. of R,S-N-(2-phenyl-2-hydroxy-1-oxoethyl)-1-methyl-3-(4-benzyloxyphenyl)propylamine in 75 ml. of THF was added dropwise over twenty minutes. The reaction mixture was heated at reflux for four hours, and then cooled to room temperature and stirred for an additional twelve hours. Excess methanol next was added to the reaction mixture in order to decompose any unreacted diborane. Concentration of the reaction mixture by evaporation of the solvent under reduced pressure provided an oily residue. The oil was dissolved in 100 ml. of methanol and 100 ml. of diethyl ether. The solution was stirred and hydrogen chloride was bubbled through the solution, thus forming a precipitate. The precipitate was collected by filtration and recrystallized from acetonitrile. The crystalline solid so formed was suspended in ethyl acetate and washed with sodium carbonate and water. After drying the ethyl acetate solution, the solvent was removed by evaporation under reduced pressure, thus affording R,S-N-(2-phenyl-2-hydroxyethyl)-1-methyl-3-(4-benzyloxyphenyl)-propylamine. M.P. 113°-115.5° C. $[\alpha]_D$ −17.5° (MeOH).

Analysis calc. for $C_{25}H_{29}NO_2$; Theory: C, 79.96; H, 7.78; N, 3.73. Found: C, 79.74; H, 7.82; N, 3.43.

A solution of 5.9 g. of the amine thus formed in 50 ml. of methanol was stirred at 24° C. while a solution of excess hydrogen chloride gas in diethyl ether was added in one portion. The precipitated solid which immediately formed was collected by filtration and then was recrystallized from acetonitrile and diethyl ether, providing 6.39 g. of the amine as the hydrochloride salt. M.P. 158.0°-160.5° C. $[\alpha]_D$ −36.1° (MeOH).

Analysis calc. for $C_{25}H_{30}ClNO_2$; Theory: C, 72.89; H, 7.34; N, 3.40. Found: C, 72.91; H, 7.34; N, 3.27.

A solution of 10.6 g. of R,S-N-(2-phenyl-2-hydroxyethyl)-1-methyl-3-(4-benzyloxyphenyl)propylaminium chloride in 140 ml. of methanol was stirred while 1.0 g. of a five percent suspension of palladium on carbon was added portionwise. The reaction mixture then was stirred for four hours at 60° C. under a hydrogen gas atmosphere at 50 p.s.i. The reaction mixture then was filtered, and the filtrate was concentrated by evaporation of the solvent under reduced pressure, thus providing 10.6 g. of a pink foam. The foam was dissolved in 600 ml. of water and stirred while a solution of 35 g. of sodium carbonate in 300 ml. of water was added portionwise over ten minutes. The product precipitated out of the aqueous alkaline solution and was collected by filtration. Recrystallization of the solid product so formed twice from 450 ml. of hot ethyl acetate provided 6.63 g. of R,S-N-(2-phenyl-2-hydroxyethyl)-1-methyl-3-(4-hydroxyphenyl)propylamine. M.P. 169.5°-173° C. $[\alpha]_D$ −24.5° (MeOH).

Analysis calc. for $C_{18}H_{23}NO_2$; Theory: C, 75.76; H, 8.12; N, 4.91. Found: C, 75.99; H, 8.11; N, 4.68.

EXAMPLE 11

R,S-N-(2-Phenyl-2-hydroxyethyl)-1-methyl-3-(4-hydroxyphenyl)propylaminium chloride A solution of 6.63 g. of the free amine from Example 10 in 200 ml. of methanol was stirred while a solution of hydrogen chloride in diethyl ether was added in one portion. The solvent was removed by evaporation under reduced pressure to provide the product as a white solid. The solid was collected by filtration and then was recrystallized from acetone and diethyl ether to afford R,S-N-(2-phenyl-2-hydroxyethyl)-1-methyl-3-(4-hydroxyphenyl)propylaminium chloride. M.P. 150°–159° C. $[\alpha]_D$ −47.0° (MeOH).

Analysis calc. for $C_{18}H_{24}ClNO_2$; Theory: C, 67.17; H, 7.52; N, 4.35; Cl, 11.02. Found: C, 66.97; H, 7.29; N, 4.50; Cl, 11.32.

EXAMPLE 12

R,S-N-(2-Phenyl-2-hydroxyethyl)-1-methyl-3-(4-acetoxyphenyl)propylamine

A solution of 6.03 g. of R,S-N-(2-phenyl-2-hydroxyethyl)-1-methyl-3-(4-hydroxyphenyl)propylamine dissolved in 350 ml. of tetrahydrofuran and 200 ml. of benzene was stirred at room temperature while 9.05 g. of triethylamine was added in one portion. The reaction mixture was stirred while a solution of 4.97 g. of thionyl chloride in 100 ml. of benzene was added dropwise over eight minutes. An additional 3.62 g. of triethylamine dissolved in 50 ml. of benzene was added to the reaction mixture, and then the reaction mixture was stirred for two hours at room temperature. The reaction mixture was washed several times with aqueous saturated sodium bicarbonate solution, and then with water. The solvent was removed from the reaction mixture by evaporation under reduced pressure to provide 8.1 g. of R,S-N-[1-methyl-3-(4-hydroxyphenyl)propyl]-5-phenyl-1-oxo-4,5-dihydro-1,2,3-oxathiazole as an orange oil.

A solution of 3.6 g. of the above-named oil in 20 ml. of benzene was stirred at room temperature while 1.5 ml. of pyridine was added, followed by the addition to the reaction mixture of 1.15 ml. of acetic anhydride. The reaction mixture was refluxed and stirred for one hour. The reaction mixture was cooled to room temperature and allowed to stand for twelve hours. The reaction mixture was next poured into 50 ml. of xylene, and the solvents were then removed by evaporation under reduced pressure to provide an oil. The oil was chromatographed over 25 g. of alumina, eluting with benzene and 80% benzene in ethyl acetate. Collection of the appropriate fractions and evaporation of the solvent therefrom gave 2.41 g. of an oil. A solution of 2.41 g. of the oil in 50 ml. of ethyl alcohol containing 4.5 ml. of 3 N hydrochloric acid was stirred for fifteen minutes at room temperature. The reaction mixture was then poured into 50 ml. of xylene, and the solvents were removed by evaporation under reduced pressure, providing 2.17 g. of a solid residue. Crystallization from ethyl acetate of the solid residue thus formed provided 1.77 g. of R,S-N-(2-phenyl-2-hydroxyethyl)-1-methyl-3-(4-acetoxyphenyl)propylaminium chloride. M.P. 160°–161° C. $[\alpha]_D$ −44° (MeOH).

Analysis calc. for $C_{20}H_{26}ClNO_3$; Theory: C, 66.02; H, 7.20; N, 3.85; Cl, 9.74. Found: C, 65.92; H, 7.31; N, 3.86; Cl, 9.78.

EXAMPLE 13

R,S-N-(2-Phenyl-2-hydroxyethyl)-1-methyl-3-(4-isobutyroxyphenyl)propylamine

A solution of 4.5 g. of R,S-N-[1-methyl-3-(4-hydroxyphenyl)propyl]-5-phenyl-1-oxo-4,5-dihydro-1,2,3-oxathioazole in 40 ml. of benzene was stirred at room temperature while 4.0 ml. of pyridine and 2.85 g. of isobutyric anhydride were added in one portion. The reaction mixture was stirred and heated at reflux for sixteen hours. The reaction mixture was cooled and diluted with xylene, and the solvents were removed by evaporation under reduced pressure, providing 4.36 g. of an oil. The oil so formed was dissolved in 8 ml. of 3 N hydrochloric acid, and the mixture was stirred for fifteen minutes at room temperature. The reaction mixture was next poured into 50 ml. of xylene, and concentrated to dryness under reduced pressure, providing 4.34 g. of a solid residue. The solid thus formed was crystallized from acetonitrile to afford 3.75 g. of R,S-N-(2-phenyl-2-hydroxyethyl)-1-methyl-3-(4-isobutyroxyphenyl)-propylaminium chloride. M.P. 158.5°–160° C. $[\alpha]_D$ −41.6° (MeOH).

Analysis calc. for $C_{22}H_{30}ClNO_3$; Theory: C, 67.42; H, 7.72; N, 3.57; Cl, 9.05. Found: C, 67.61; H, 8.01; N, 3.74; Cl, 9.16.

EXAMPLE 14

R,S-N-(2-Phenyl-2-hydroxyethyl)-1-methyl-3-(4-methoxycarbonylphenyl)propylamine Methyl 2-(4-hydroxycarbonylphenyl)ethyl ketone was esterified by reaction with methyl alcohol and hydrochloric acid to provide methyl 2-(4-methoxycarbonylphenyl)ethyl ketone. The ketone was condensed with optically active S-α-methylbenzylamine, and the imine which was formed was reduced to provide N-(α-methylbenzyl)-1-methyl-3-(4-methoxycarbonylphenyl)-propylamine. The amine was converted to the hydrochloride salt, and fractional crystallization of the salt thus formed afforded optically active S-N-(α-methylbenzyl)-1-methyl-3-(4-methoxycarbonylphenyl)-propylaminium chloride. M.P. 198°–205° C. $[\alpha]_D$ −81.2° (MeOH).

The resolved α-methylbenzyl protected aminium chloride was hydrogenated in the presence of Raney nickel to effect removal of the α-methylbenzyl protecting group, thus providing optically active S-1-methyl-3-(4-methoxycarbonylphenyl)propylaminium chloride. M.P. 165°–172° C. $[\alpha]_D$ −6.7° (MeOH).

A solution of S-1-methyl-3-(4-methoxycarbonylphenyl)propylaminium chloride in ethyl acetate was reacted with aqueous sodium carbonate to provide 4.8 g. of S-1-methyl-3-(4-methoxycarbonylphenyl)propylamine. The optically active free amine was dissolved in a solution of 150 ml. of N,N-dimethylformamide containing 3.52 g. of R-mandelic acid and 3.4 g. of 1-hydroxybenzotriazole. The reaction mixture was stirred while a solution of 4.78 g. of N,N'-dicyclohexylcarbodiimide in 50 ml. of DMF was added dropwise over twenty minutes. Following the complete addition of the dicyclohexylcarbodiimide, the reaction mixture was cooled to about 10° C. and stored for twelve hours at that temperature. The dicyclohexylurea which had precipitated out of the reaction solution was removed by filtration, and the filtrate was concentrated to dryness by evaporation of the solvent under reduced pressure to provide an oil. The oil so formed was dissolved in ethyl acetate and washed with aqueous sodium carbonate, with water, and dried. Evaporation of the solvent under reduced pressure afforded an oil which was crystallized from diethyl ether and hexane to provide 6.27 g. of R,S-(2-phenyl-2-hydroxy-1-oxoethyl)-1-methyl-3-(4-methoxycarbonylphenyl)propylamine. M.P. 99°–101° C. $[\alpha]_D$ −59.2° (MeOH).

Analysis calc. for $C_{20}H_{23}NO_4$; Theory: C, 70.36; H, 6.79; N, 4.10. Found: C, 70.57; H, 6.85; N, 4.21.

The above reactions were repeated on several occasions to provide additional quantities of the amide. To a stirred solution of 26.2 g. of R,S-N-(2-phenyl-2-hydroxy-1-oxoethyl)-1-methyl-3-(4-methoxycarbonylphenyl)propylamine in 300 ml. of tetrahydrofuran was added portionwise over one hour 400 ml. of a 1.02 N solution of diborane in tetrahydrofuran. Following the addition, the reaction mixture was stirred at 25° C. for twenty-six hours. The reaction mixture next was diluted by the addition of 250 ml. of methanol. Removal of the reaction solvent by evaporation under reduced pressure provided the product as a crude oil. The oil was dissolved in 50 ml. of fresh methanol, and the solution was diluted with 100 ml. of diethyl ether saturated with hydrogen chloride, thereby forming the hydrochloride salt of the product as a white solid. The solid was recrystallized from 100 ml. of acetonitrile to provide 15.60 g. of R,S-N-(2-phenyl-2-hydroxyethyl)-1-methyl-3-(4-methoxycarbonylphenyl)propylaminium chloride. M.P. 141°–155° C. The salt was converted to the free amine base which was crystallized from ethyl acetate. M.P. 125°–128° C. The free base was converted to the hydrochloride salt, which when crystallized from acetonitrile and diethyl ether afforded the desired product having a M.P. 149°–154° C. $[\alpha]_D$ −48.8° (MeOH).

Analysis calc. for $C_{20}H_{26}ClNO_3$; Theory: C, 66.02; H, 7.20; N, 3.85. Found: C, 65.91; H, 6.96; N, 3.78

EXAMPLE 15

R,S-N-(2-Phenyl-2-hydroxyethyl)-1-methyl-3-(4-aminocarbonylphenyl)propylamine

A solution of 1.21 g. of R,S-N-(2-phenyl-2-hydroxyethyl)-1-methyl-3-(4-methoxycarbonylphenyl)propylamine in 60 ml. of ethyl alcohol containing 20 ml. of anhydrous hydrazine was stirred and heated at reflux for twenty-eight hours. The reaction mixture then was cooled to room temperature and the solvent was removed therefrom by evaporation under reduced pressure to provide a product which was crystallized from isopropanol to give 940 mg. of R,S-N-(2-phenyl-2-hydroxyethyl)-1-methyl-3-(4-hydrazinocarbonylphenyl)propylamine. M.P. 134°–142° C. $[\alpha]_D$ −27.9° (MeOH).

Analysis calc. for $C_{19}H_{25}N_3O_2$; Theory: C, 69.70; H, 7.70; N, 12.83. Found: C, 69.72; H, 7.44; N, 12.97.

A solution of 720 mg. of R,S-N-(2-phenyl-2-hydroxyethyl)-1-methyl-3-(4-hydrazinocarbonylphenyl)-propylamine in 100 ml. of ethanol containing 8 g. of Raney nickel was hydrogenated in a Brown hydrogenation apparatus utilizing 4 g. of sodium borohydride as the hydrogen source. The reaction mixture was stirred at 25° C. for twelve hours, and then was filtered through hyflo super cell. The filtrate was evaporated to dryness under reduced pressure to provide a solid. The solid residue thus formed was dissolved in 50 ml. of water containing 25 ml. of 3 N hydrochloric acid. The aqueous acid solution was washed with ethyl acetate, and then made basic by the gradual addition of ammonium hydroxide. The aqueous alkaline solution was extracted several times with fresh portions of ethyl acetate. The organic extracts were combined, washed with water and dried. Removal of the solvent by evaporation under reduced pressure provided, as a white solid, R,S-N-(2-phenyl-2-hydroxyethyl)-1-methyl-3-(4-aminocarbonylphenyl)propylamine. The solid thus formed was dissolved in methanol and the solution was diluted with 30 ml. of diethyl ether saturated with hydrogen chloride. Filtration of the precipitated solid which formed afforded 72.6 mg. of R,S-N-(2-phenyl-2-hydroxyethyl)-1-methyl-3-(4-aminocarbonylphenyl)-propylaminium chloride. M.P. 229°–230° C. $[\alpha]_D$ −51.6° (MeOH).

Analysis calc. for $C_{19}H_{25}ClN_2O_2$; Theory: C, 65.41; H, 7.22; N, 8.03; Cl, 10.16. Found: C, 65.29; H, 7.14; N, 8.24; Cl, 10.04.

EXAMPLE 16 dl-N-(2-Phenyl-2-hydroxyethyl)-3-(4-methoxycarbonylphenyl)propylamine

A solution of 7.0 g of 3-(4-methoxycarbonylphenyl)-propylamine in 75 ml. of ethanol containing 4.8 g. of dl-styrene oxide was heated to reflux and stirred for seven hours. The reaction mixture was cooled to room temperature and the solvent was removed by evaporation under reduced pressure to provide the product as a solid residue. The residue was crystallized from diethyl ether to afford 1.7 g. of dl-N-(2-phenyl-2-hydroxyethyl)-3-(4-methoxycarbonylphenyl)propylamine. M.P. 109°–112° C. The amine so formed was converted to the hydrochloride salt by reaction with hydrogen chloride in methanol to afford 1.3 g. of dl-N-(2-phenyl-2-hydroxyethyl)-3-(4-methoxycarbonylphenyl)propylaminium chloride. M.P. 179°–181° C.

Analysis calc. for $C_{19}H_{24}NO_3Cl$; Theory: C, 65.23; H, 6.91; N, 4.00. Found: C, 65.49; H, 6.79; N, 3.97.

The mixture of optical isomers thus formed can be used as a mixture since the S-isomer is substantially devoid of biological activity. If desired, however, the racemic mixture can be resolved by standard procedures.

EXAMPLE 17 dl-N-(2-Phenyl-2-hydroxyethyl)-3-(4-aminocarbonylphenyl)propylamine

A solution of 3.4 g. of dl-N-(2-phenyl-2-hydroxyethyl)-3-(4-methoxycarbonylphenyl)propylamine in 200 ml. of ethanol containing 50 ml. of hydrazine was heated to reflux and stirred for twelve hours. The reaction mixture was cooled to room temperature and concentrated to dryness by evaporation of the solvent. The residue was crystallized from ethanol to give 3.0 g. of dl-N-(2-phenyl-2-hydroxyethyl)-3-(4-hydrazinocarbonylphenyl)propylamine. M.P. 143°–145° C.

Analysis calc. for $C_{18}H_{23}N_3O_2$; Theory: C, 68.98; H, 7.40; N, 13.41. Found: C, 69.25; H, 7.45; N, 13.55.

A solution of 3.0 g. of dl-N-(2-phenyl-2-hydroxyethyl-3-(4-hydrazinocarbonylphenyl)propylamine in 500 ml. of ethanol was stirred at 25° C. for seventy-two hours under hydrogen in a Brown hydrogenator and in the presence of four teaspoons full of Raney nickel. Additional catalyst was added to the reaction mixture and stirring was continued for twelve hours. The reaction mixture then was filtered and the solvent was removed from the filtrate by evaporation under reduced pressure to provide a solid residue. The residue was dissolved in ethyl acetate, washed with dilute ammonium hydroxide, with water and dried. Evaporation of the solvent under reduced pressure provided a solid which next was crystallized from methanol to provide 600 mg. of dl-N-(2-phenyl-2-hydroxyethyl)-3-(4-aminocarbonylphenyl)propylamine. M.P. 138°–140° C. The amine so formed was converted to the hydrochloride salt by reaction with hydrogen chloride in methanol to provide 600 mg. of dl-N-(2-phenyl-2-hydroxyethyl)-3-(4-aminocarbonylphenyl)propylaminium chloride. M.P. 230°–232° C.

Analysis calc. for $C_{18}H_{23}N_2O_2Cl$; Theory: C, 64.57; H, 6.92; N, 8.37. Found: C, 64.64; H, 6.55; N, 8.51.

As described in Example 16, the racemic mixture thus formed can be utilized as such or can be separated by standard procedures.

EXAMPLE 18

R,S-N-(2-Phenyl-2-hydroxyethyl)-1-methyl-3-(4-aminocarbonylphenyl)propylaminium chloride To a refluxing solution of 109.6 g. of S-1-methyl-3-(4-aminocarbonylphenyl)propylamine in 600 ml. of ethanol and 200 ml. of methanol was added dropwise over one hour a solution of 68.4 g. of R-styrene oxide in 100 ml. of ethanol. The reaction mixture was heated at reflux for three hours following complete addition of the styrene oxide, and then was cooled to room temperature and concentrated by evaporation of the solvent under reduced pressure. The reaction mixture next was diluted by the addition of 200 ml. of diethyl ether and filtered. The precipitate was triturated with water, dried, and recrystallized from acetonitrile to provide 72.6 g. of the free amine product as a solid. The amine so formed was converted to the hydrochloride salt by reaction with hydrogen chloride in diethyl ether to provide 64.0 g. of R,S-N-(2-phenyl-2-hydroxyethyl)-1-methyl-3-(4-aminocarbonylphenyl)propylaminium chloride. M.P. 229°–231° C. $[\alpha]_D$ −52.1° (MeOH).

Analysis calc. for $C_{19}H_{25}ClN_2O_2$; Theory: C, 65.41; H, 7.22; N, 8.03. Found: C, 65.17; H, 7.10; N, 8.03.

EXAMPLE 19

R,S-N-(2-Phenyl-2-hydroxyethyl)-1-methyl-3-(4-hydroxyphenyl)propylamine

A mixture of 100 g. of R-mandelic acid and 244 ml. of dichloracetyl chloride was heated at 60° C. and stirred for three hours. The mixture then was cooled to room temperature and concentrated in volume under reduced pressure to provide a yellow oil. The oil was dissolved in 200 ml. of thionyl chloride, and the reaction mixture was heated to reflux and stirred for four hours. The reaction mixture was cooled to room temperature and excess thionyl chloride was removed by evaporation under reduced pressure. The product was purified by distillation to provide 180.9 g. of R-(2-phenyl-2-dichloroacetoxy)acetyl chloride. B.P. 112.5° C. (0.08 torr); $[\alpha]_D$ −191° (toluene).

A solution of 4.3 g. of S-1-methyl-3-(4-benzyloxyphenyl)propylamine in 70 ml. of dichloromethane was added in one portion to a stirred suspension of 5.5 g. of sodium bicarbonate and 5.02 g. of R-(2-phenyl-2-dichloroacetoxy)acetyl chloride in 100 ml. of dichloromethane. The reaction mixture was stirred at room temperature for sixteen hours and then filtered. The filtrate was concentrated by evaporation of the solvent under reduced pressure to provide a solid residue. The residue was crystallized from 75 ml. of diethyl ether to afford 6.70 g. of R,S-N-(2-phenyl-2-dichloroacetoxy-1-oxoethyl)-1-methyl-3-(4-benzyloxyphenyl)propylamine. M.P. 110°–111.5° C. $[\alpha]_D$ −41.7° (MeOH).

Analysis calc. for $C_{27}H_{27}Cl_2NO_4$; Theory: C, 64.80; H, 5.44; N, 2.80; Cl, 14.17. Found: C, 64.66; H, 5.61; N, 2.94; Cl, 14.42.

A solution of 6.70 g. of the amide thus formed in 130 ml. of tetrahydrofuran containing 50 ml. of 1 N diborane in tetrahydrofuran was heated to reflux and stirred for twenty hours. The reaction mixture was cooled to 60° C. and decomposed by the dropwise addition of 2 ml. of water and 35 ml. of 3 N hydrochloric acid. The aqueous acidic mixture was heated to reflux for two hours, again cooled to about 40° C., and then made alkaline by the addition of 100 ml. of 5 N sodium hydroxide. After stirring the alkaline mixture for two hours at room temperature, the organic layer was separated and the aqueous alkaline layer was extracted with ethyl acetate. The organic layers were combined, washed with brine, dried and the solvent was evaporated to provide 5.1 g. of a solid residue. The solid was dissolved in 100 ml. of hot ethanol and acidified by the addition of a diethyl ether solution of hydrogen chloride. The crystalline precipitate which formed was collected by filtration and dried to provide 4.40 g. of R,S-N-(2-phenyl-2-hydroxyethyl)-1-methyl-3-(4-benzyloxyphenyl)propylaminium chloride. M.P. 160°–162.5° C. $[\alpha]_D$ −37.8° (MeOH).

Analysis calc for $C_{25}H_{30}ClNO_2$; Theory: C, 72.89; H, 7.34; N, 3.40; Cl, 8.61. Found: C, 73.02; H, 7.58; N, 3.64; Cl, 8.96.

Hydrogenolysis of 4.28 g. of the amine salt thus formed in the presence of 500 mg. of five percent palladium on carbon in methanol for three hours at 40° C. effected removal of the benzyl protecting group to provide, after purification by crystallization from acetone and diethyl ether, 2.79 g. of R,S-N-(2-phenyl-2-hydroxyethyl)-1-methyl-3-(4-hydroxyphenyl)propylaminium chloride. M.P. 153°–154° C. $[\alpha]_D$ −49.9° (MeOH).

Analysis calc. for $C_{18}H_{24}ClNO_2$; Theory: C, 67.17; H, 7.52; N, 4.35; Cl, 11.02. Found: C, 67.08; H, 7.33; N, 4.51; Cl, 11.37.

EXAMPLE 20

Preparation of 250 mg. Tablets

| | |
|---|---|
| R,S—N—(2-phenyl-2-hydroxyethyl)-1-methyl-3-(4-aminocarbonylphenyl)-propylaminium chloride | 250 mg. |
| Lactose | 200 mg. |
| Corn Starch | 300 mg. |
| Corn Starch Paste | 50 mg. |
| Calcium Stearate | 5 mg. |
| Dicalcium Phosphate | 45 mg. |

The active drug, corn starch, lactose, and dicalcium phosphate are uniformly blended. The corn starch paste is prepared as a 10 percent aqueous paste and is blended into the mixture to uniformity. The mixture is blended with the calcium stearate and then compressed into tablets. Such tablets can be administered to an obese subject at the rate of 1 to about 4 tablets per day or as needed.

EXAMPLE 21

Preparation for Suppositories

| | |
|---|---|
| R,S—N—(2-phenyl-2-hydroxyethyl)-1-methyl-3-(4-hydroxyphenyl)propylaminium chloride | 500 mg. |
| Theobroma oil | 1500 mg. |

The above ingredients are blended to uniformity at a temperature of about 60° C. and then permitted to cool in a tapered mold. Each suppository will weigh about 2 grams and can be administered to a mature obese subject from 1 to 2 times each day for the reduction of weight, or to an immature obese subject for the control of weight gain.

EXAMPLE 22

Preparation for Oral Suspension

| | |
|---|---|
| R,S—N—[2-(2-fluorophenyl)-2-hydroxyethyl]-1-methyl-3-(4-hydroxyphenyl)-propylaminium acetate | 5000 mg. |
| Sorbitol solution (70% N.F.) | 40 ml. |
| Sodium benzoate | 150 mg. |
| Lactose | 10 mg. |
| Cherry flavor | 50 mg. |
| Distilled water q.s. ad | 100 ml. |

The sorbitol solution is added to 40 ml. of distilled water and the R,S-N-[2-(2-fluorophenyl)-2-hydroxyethyl]-1-methyl-3-(4-hydroxyphenyl)propylaminium acetate is dissolved therein. The lactose, sodium benzoate and flavoring are added and dissolved. The volume of the solution is adjusted to 100 ml. with distilled water. Each ml. of syrup contains 50 mg. of active drug. A mature obese mammal will be administered about 5 to about 20 ml. of syrup each day for the effective loss of weight.

EXAMPLE 23

Feed additive for swine

A compound such as dl-N-(2-phenyl-2-hydroxyethyl)-3-(4-methylaminocarbonylphenyl)propylaminium chloride is added to a standard feed ration for grower pigs at the rate of about 40 to about 100 g. per ton of feed. Such mixture is then fed to the animals at normal rations for the production of pork products having improved meat quality, ie. improved leanness.

We claim:

1. A pharmaceutical formulation useful in the control of weight in obese animals comprising as active principle an amount effective for controlling weight of an optically active phenethanolamine of the formula

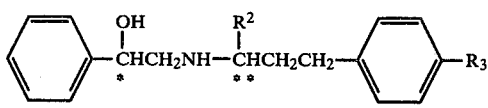

wherein:
$R_2$ is hydrogen, methyl or ethyl;
$R_3$ is aminocarbonyl or methylaminocarbonyl;
$\underset{*}{C}$ is an asymmetric carbon atom having the R absolute stereochemical configuration;
$\underset{**}{C}$ is an asymmetric carbon atom when $R_2$ is methyl or ethyl, and when asymmetric is of the S absolute stereochemical configuration; and the non-toxic pharmaceutically acceptable acid addition salts thereof, in combination with a suitable pharmaceutical carrier therefor.

2. The formulation of claim 1 wherein $R_2$ is methyl.

3. The formulation of claim 2 employing R,S-N-(2-phenyl-2-hydroxyethyl)-1-methyl-3(4-methylaminocarbonylphenyl)propylamine.

4. The formulation of claim 2 wherein the active principle is R,S-N-(2-phenyl-2-hydroxyethyl)-1-methyl-3-(4-aminocarbonylphenyl)propylamine.

5. The formulation of claim 1 wherein $R_2$ is hydrogen.

6. A method for effecting weight control in an obese animal in need of treatment which comprises administering to such animal an amount effective for controlling weight of a compound of the formula

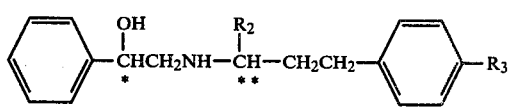

wherein:
$R_2$ is hydrogen, methyl or ethyl;
$R_3$ is aminocarbonyl or methylaminocarbonyl;
$\underset{*}{C}$ is an asymmetric carbon atom having the R absolute stereochemical configuration;
$\underset{**}{C}$ is an asymmetric carbon atom when $R_2$ is methyl or ethyl, and when asymmetric is of the S absolute stereochemical configuration; and the non-toxic pharmaceutically acceptable acid addition salts thereof.

7. A method according to claim 3 wherein a compound is administered to a mature obese animal effect a weight loss.

8. A method according to claim 6 wherein a compound is administered to an immature obese animal to prevent excessive weight gain.

9. The method of claim 6 employing a compound wherein $R_2$ is methyl or ethyl.

10. The method of claim 9 wherein the active principle administered in R,S-N-(2-phenyl-2-hydroxyethyl)-1-methyl-3-(4-methylaminocarbonylphenyl)propylamine.

11. The method according to claim 9 wherein the active principle administered is R,S-N-(2-phenyl-2-hydroxyethyl)-1-methyl-3-(4-aminocarbonylphenyl)-propylamine.

12. The method of claim 6 employing a compound wherein $R_2$ is hydrogen.

13. A method for improving the leanness of meat in livestock animals comprising administering an effective amount of a compound of the formula

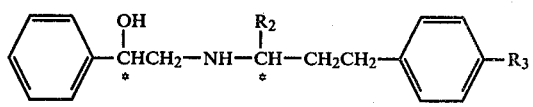

wherein:
$R_2$ is hydrogen, methyl or ethyl;
$R_3$ is aminocarbonyl or methylaminocarbonyl;
$\underset{*}{C}$ is an asymmetric carbon atom having the R absolute stereochemical configuration;
$\underset{**}{C}$ is an asymmetric carbon atom when $R_2$ is methyl or ethyl, and when asymmetric is of the S absolute stereochemical configuration; and the non-toxic pharmaceutically acceptable acid addition salts thereof.

14. The method of claim 13 wherein the animal species treated is swine.

15. The method of claim 13 employing a compound wherein $R_2$ is hydrogen.

16. The method of claim 15 wherein the compound administered is dl-N-(2-phenyl-2-hydroxyethyl)-3-(4-methylaminocarbonylphenyl)propylamine.

17. The method of claim 15 wherein the compound administered is dl-N-(2-phenyl-2-hydroxyethyl)-3-(4-aminocarbonylphenyl)propylamine.

18. The method of claim 13 employing a compound wherein $R_2$ is methyl or ethyl.

19. The method of claim 18 wherein the compound administered is R,S-N-(2-phenyl-2-hydroxyethyl)-1-methyl-3-(4-aminocarbonylphenyl)propylamine.

20. The method of claim 18 wherein the compound administered is R,S-N-(2-phenyl-2-hydroxyethyl)-1-methyl-3-(4-methylaminocarbonylphenyl)propylamine.

* * * * *